(12) United States Patent
Yue et al.

(10) Patent No.: US 12,102,634 B2
(45) Date of Patent: Oct. 1, 2024

(54) USE OF BERBAMINE OR ITS ANALOGUE FOR PREVENTING OR TREATING RNA VIRUS INFECTION

(71) Applicants: City University of Hong Kong, Kowloon (HK); 6J Biotechnology (Hong Kong) Limited, Science Park (HK)

(72) Inventors: Jianbo Yue, Kowloon Tong (HK); Lihong Huang, Kowloon Tong (HK); Qingru Zhang, Science Park (HK)

(73) Assignees: 6J Biotechnology (Hong Kong) Limited, Science Park (HK); City University of Hong Kong, Kowloon (HK)

( * ) Notice: Subject to any disclaimer, the term of this patent is extended or adjusted under 35 U.S.C. 154(b) by 0 days.

(21) Appl. No.: 17/640,455

(22) PCT Filed: Sep. 4, 2020

(86) PCT No.: PCT/CN2020/113378
§ 371 (c)(1),
(2) Date: Mar. 4, 2022

(87) PCT Pub. No.: WO2021/043234
PCT Pub. Date: Mar. 11, 2021

(65) Prior Publication Data
US 2022/0378778 A1   Dec. 1, 2022

Related U.S. Application Data

(63) Continuation-in-part of application No. 16/559,869, filed on Sep. 4, 2019, now Pat. No. 11,357,771.

(60) Provisional application No. 63/026,350, filed on May 18, 2020.

(51) Int. Cl.
*A61K 31/4748* (2006.01)
*A61P 31/14* (2006.01)

(52) U.S. Cl.
CPC .......... *A61K 31/4748* (2013.01); *A61P 31/14* (2018.01)

(58) Field of Classification Search
CPC ................................................. A61K 31/4748
See application file for complete search history.

(56) References Cited

U.S. PATENT DOCUMENTS

2014/0275139 A1   9/2014  Van Dyke
2014/0378435 A1   12/2014 Davey et al.

FOREIGN PATENT DOCUMENTS

| CN | 109125323 | 7/2020 |
| CN | 111728973 | 10/2020 |
| EP | 0931544 | 7/1999 |
| WO | 2008033466 | 3/2008 |
| WO | 2011057262 | 5/2011 |

OTHER PUBLICATIONS

Shen et al., High-Throughput Screening and Identification of Potent Broad-Spectrum Inhibitors of Coronaviruses, Journal of Virology, vol. 93, No. 12, May 29, 2019.*
Patani et al., Bioisosterism: A Rational Approach in Drug Design, Chem. Rev. 1996, 96, 3147-3176.*
Smith RD. Responding to global infectious disease outbreaks: lessons from SARS on the role of risk perception, communication and management. Social science & medicine 63, 3113-3123 (2006).
Wang L-F, Shi Z, Zhang S, Field H, Daszak P, Eaton BT. Review of bats and SARS. Emerging infectious diseases 12, 1834 (2006).
Wang S-M, Liu C-C. Enterovirus 71: epidemiology, pathogenesis and management. Expert review of anti-infective therapy 7, 735-742 (2009).
Fehr AR, Perlman S. Coronaviruses: an overview of their replication and pathogenesis. In: Coronaviruses). Springer (2015).
Gralinski LE, Baric RS. Molecular pathology of emerging coronavirus infections. The Journal of pathology 235, 185-195 (2015).
Zumla A, Chan JF, Azhar EI, Hui DS, Yuen K-Y. Coronaviruses—drug discovery and therapeutic options. Nature reviews Drug discovery 15, 327 (2016).
Ksiazek TG, et al. A novel coronavirus associated with severe acute respiratory syndrome. New England journal of medicine 348, 1953-1966 (2003).
Shapiro M, London B, Nigri D, Shoss A, Zilber E, Fogel I. Middle East respiratory syndrome coronavirus: review of the current situation in the world. Disaster and military medicine 2, 9 (2016).
Gubler DJ, Clark GG. Dengue/dengue hemorrhagic fever: the emergence of a global health problem. Emerging Infectious diseases 1, 55 (1995).
Al-Qahtani AA, Nazir N, Al-Anazi MR, Rubino S, Al-Ahdal MN. Zika virus: a new pandemic threat. The Journal of Infection in Developing Countries 10, 201-207 (2016).
Lowe R, et al. The Zika virus epidemic in Brazil: from discovery to future implications. International journal of environmental research and public health 15, 96 (2018).
Waggoner JJ, Pinsky BA. Zika virus: diagnostics for an emerging pandemic threat. Journal of clinical microbiology 54, 860-867 (2016).

(Continued)

*Primary Examiner* — Svetlana M Ivanova
(74) *Attorney, Agent, or Firm* — Renner, Kenner, Greive, Bobak, Taylor & Weber

(57) ABSTRACT

A method of preventing or treating a subject suffering from a flavivirus infection caused by Japanese encephalitis virus, Zika virus, or Dengue virus by administering an effective amount of berbamine of Formula (I) or its analogue to the subject. A method of inhibiting the entry of such a flavivirus, an enterovirus and/or a lentivirus into host cells includes contacting the host cells with an effective amount of berbamine of Formula (I) or its analogue. The invention also provides a method of preventing or treating a subject suffering from a coronavirus, particularly SARS-CoV-2 or MERS-CoV, a method of inhibiting the entry of a coronavirus into host cells, as well as uses of berbamine or its analogue in the preparation of a medicament for preventing or treating a flavivirus infection, enterovirus infection, lentivirus infection or coronavirus infection.

5 Claims, 28 Drawing Sheets

(56) References Cited

OTHER PUBLICATIONS

Wang H, Liang G. Epidemiology of Japanese encephalitis: past, present, and future prospects. Therapeutics and clinical risk management 11, 435 (2015).
Campbell GL, et al. Estimated global incidence of Japanese encephalitis: a systematic review. Bulletin of the World Health Organization 89, 766-774 (2011).
Sampath A, Padmanabhan R. Molecular targets for flavivirus drug discovery. Antiviral research 81, 6-15 (2009).
Liu C-C, Tseng H-W, Wang S-M, Wang J-R, Su I-J. An outbreak of enterovirus 71 infection in Taiwan, 1998: epidemiologic and clinical manifestations. Journal of Clinical Virology 17, 23-30 (2000).
Zhou Y, Frey TK, Yang JJ. Viral calciomics: interplays between Ca2+ and virus. Cell calcium 46, 1-17 (2009).
Wang S, et al. Screening of FDA-approved drugs for inhibitors of Japanese encephalitis virus infection. Journal of virology 91, e01055-01017 (2017).
Scherbik SV, Brinton MA. Virus-induced Ca2+ influx extends survival of west nile virus-infected cells. Journal of virology 84, 8721-8731 (2010).
Haughey NJ, Mattson MP. Calcium dysregulation and neuronal apoptosis by the HIV-1 proteins Tat and gp120. Journal of acquired immune deficiency syndromes (1999) 31, S55-61 (2002).
Fujioka Y, et al. A Ca 2+-dependent signalling circuit regulates influenza A virus internalization and infection. Nature communications 4, 2763 (2013).
Fujioka Y, et al. A sialylated voltage-dependent Ca2+ channel binds hemagglutinin and mediates influenza A virus entry into mammalian cells. Cell host & microbe 23, 809-818. e805 (2018).
Bissig C, et al. Viral infection controlled by a calcium-dependent lipid-binding module in ALIX. Developmental cell 25, 364-373 (2013).
Alam M, et al. Verapamil has Antiviral Activities that Target Different Steps of the Influenza Virus Replication Cycle. J Antivir Antiretrovir 8, 121-130 (2016).
Wang W, Zhang X, Gao Q, Xu H. TRPML1: an ion channel in the lysosome. Handb Exp Pharmacol 222, 631-645 (2014).
Venkatachalam K, Wong CO, Zhu MX. The role of TRPMLs in endolysosomal trafficking and function. Cell Calcium 58, 48-56 (2015).
Weber F, Wagner V, Rasmussen SB, Hartmann R, Paludan SR. Double-stranded RNA is produced by positive-strand RNA viruses and DNA viruses but not in detectable amounts by negative-strand RNA viruses. Journal of virology 80, 5059-5064 (2006).
O'Brien CA, et al. Viral RNA intermediates as targets for detection and discovery of novel and emerging mosquito-borne viruses. PLOS neglected tropical diseases 9, (2015).
Dorobantu CM, et al. Modulation of the host lipid landscape to promote RNA virus replication: the picornavirus encephalomyocarditis virus converges on the pathway used by hepatitis C virus. PLoS pathogens 11, (2015).
Bhagya N, Chandrashekar KR. Tetrandrine—A molecule of wide bioactivity. Phytochemistry 125, 5-13 (2016).
Wang G, Lemos JR, Iadecola C. Herbal alkaloid tetrandrine: fron an ion channel blocker to inhibitor of tumor proliferation. Trends Pharmacol Sci 25, 120-123 (2004).
Sakurai Y, et al. Ebola virus. Two-pore channels control Ebola virus host cell entry and are drug targets for disease treatment. Science 347, 995-998 (2015).
Monazahian M, et al. Low density lipoprotein receptor as a candidate receptor for hepatitis C virus. J Med Virol 57, 223-229 (1999).
Wunschmann S, Medh JD, Klinzmann D, Schmidt WN, Stapleton JT. Characterization of hepatitis C virus (HCV) and HCV E2 interactions with CD81 and the low-density lipoprotein receptor. J Virol 74, 10055-10062 (2000).
Finkelshtein D, Werman A, Novick D, Barak S, Rubinstein M. LDL receptor and its family members serve as the cellular receptors for vesicular stomatitis virus. Proc Natl Acad Sci U S A 110, 7306-7311 (2013).
Fischer DG, Tal N, Novick D, Barak S, Rubinstein M. An antiviral soluble form of the LDL receptor induced by Interferon. Science 262, 250-253 (1993).
Bochkov YA, Gern JE. Rhinoviruses and Their Receptors: Implications for Allergic Disease. Curr Allergy Asthma Rep 16, 30 (2016).
Hoffmann M, et al. SARS-COV-2 Cell Entry Depends on ACE2 and TMPRSS2 and Is Blocked by a Clinically Proven Protease Inhibitor. Cell 181, 271-280 e278 (2020).
Raj VS, et al. Dipeptidyl peptidase 4 is a functional receptor for the emerging human coronavirus—EMC. Nature 495, 251-254 (2013).
Powelka AM, et al. Stimulation-dependent recycling of integrin beta1 regulated by ARF6 and Rab11. Traffic 5, 20-36 (2004).
Jackson T, et al. Arginine-glycine-aspartic acid-specific binding by foot-and-mouth disease viruses to the purified Integrin alpha (v) beta3 in vitro. Journal of Virology 71, 8357-8361 (1997).
Gianni T, Gatta V, Campadelli-Fiume G. αVβ3-integrin routes herpes simplex virus to an entry pathway dependent on cholesterol-rich lipid rafts and dynamin2. Proceedings of the National Academy of Sciences 107, 22260-22265 (2010).
Chu JJ-h, Ng M-L. Interaction of West Nile virus with αvβ3 integrin mediates virus entry into cells. Journal of Biological Chemistry 279, 54533-54541 (2004).
Chu J, Ng M. Characterization of a 105-kDa plasma membrane associated glycoprotein that is involved in West Nile virus binding and infection. Virology 312, 458-469 (2003).
Berinstein A, Roivainen M, Hovi T, Mason P, Baxt B. Antibodies to the vitronectin receptor (integrin alpha V beta 3) Inhibit binding and infection of foot-and-mouth disease virus to cultured cells. Journal of virology 69, 2664-2666 (1995).
Westhaus S, et al. Scavenger receptor class B member 1 (SCARB1) variants modulate hepatitis C virus replication cycle and viral load. Journal of hepatology 67, 237-245 (2017).
Li Y, Kakinami C, Li Q, Yang B, Li H. Human apolipoprotein AI is associated with dengue virus and enhances virus Infection through SR-BI. PloS one 8, (2013).
Monazahian M, et al. Low density lipoprotein receptor as a candidate receptor for hepatitis C virus. Journal of medical virology 57, 223-229 (1999).
Molina S, et al. The low-density lipoprotein receptor plays a role in the infection of primary human hepatocytes by hepatitis C virus. Journal of hepatology 46, 411-419 (2007).
Hofer F, et al. Members of the low density lipoprotein receptor family mediate cell entry of a minor-group common cold virus. Proceedings of the National Academy of Sciences 91, 1839-1842 (1994).
Huang, L.H et al., "Berbamine inhibits the infection of DARS-CoV-2 and flaviviruses by compromising TPRMLs-mediated endolysosomal trafficking of viral receptors" Reseach Square, May 26, 2020 (May 26, 2020), pp. 1-29.
Kim, D.E. et al., "Natural Bis-Benzylisoquinoline Alkaloids Tetrandrine, Fangchioline, and Cepharanthine, Inhibit Human Coronavirus OC43 Infextion of MRC-5 Humean Lung Cells.". Biomolecules. vol. 9, No. 696, Nov. 4, 2019 (Nov. 4, 2019), pp. 1-16.
Jeon, S. et al., "Identification of antiviral drug candidates against SARS-CoV-2 from FDA-approved drugs.". Bio. Rxiv. , Mar. 28, 2020 (Mar. 28, 2020), pp. 1-20.
Liou, J.T. et al., "Differential effects of triptolide and tetrandrine on activation of COX-2, NF-kappaB, and AP-1 and virus production in dengue virus-infected human lung cells.", European Journal of Pharmacology., vol. 589, No. 1-3, May 6, 2006 (May 6, 2006), pp. 268-298.
Gunaratine, G.S. et al, "A screening campaign in sea urchin egg homogenate as a platform for discovering modulators of NAADP-dependent Ca 2+ signaling in human cells." Cell Calcium., vol. 75, Aug. 16, 2018 (Aug. 16, 2018), pp. 42-52.
Shen, L. et al., "High-Throughput Screening and Identification of Potent Broad-Spectrum Inhibitors of Coronaviruses." Journal of Virology., vol. 93, No. 12, May 29, 2019 (May 29, 2019), pp. 1-15.
Written Opinion of the International Searching Authority in PCT/CN2020/113378 mailed Dec. 8, 2020.
Solomon, T., and Mallewa, M. (2001). Dengue and other emerging flaviviruses. J Infect 42, 104-115.

(56) References Cited

OTHER PUBLICATIONS

Katzelnick, L.C., Coloma, J., and Harris, E. (2017). Dengue: knowledge gaps, unmet needs, and research priorities. Lancet Infect Dis 17, e88-e100.
Murrell, S., Wu, S.C., and Butler, M. (2011). Review of dengue virus and the development of a vaccine. Biotechnol Adv 29, 239-247.
Endy, T.P., and Nisalak, A. (2002). Japanese encephalitis virus: ecology and epidemiology. Curr Top Microbiol Immunol 267, 11-48.
Cheng, V.C.C., Sridhar, S., Wong, S.C., Wong, S.C.Y., Chan, J.F.W., Yip, C.C.Y., Chau, C.H., Au, T.W.K., Hwang, Y. Y., Yau, C.S.W., et al. (2018). Japanese Encephalitis Virus Transmitted via Blood Transfusion, Hong Kong, China. Emerg Infect Dis 24.
Wang, Z., Wang, P., and An, J. (2016). Zika virus and Zika fever. Virol Sin 31, 103-109.
Chang, C., Ortiz, K., Ansari, A., and Gershwin, M.E. (2016). The Zika outbreak of the 21st century. J Autoimmun 68, 1-13.
Michos, A.G., Syriopoulou, V.P., Hadjichristodoulou, C., 'Daikos, G.L., Lagona, E., 'Douridas', P., Mostrou, G., and Theodoridou, M. (2007). Aseptic meningitis in children: analysis of 506 cases. PloS one 2, e674.
Klingel, K., Hohenadl, C., Canu, A., Albrecht, M., Seemann, M., Mall, G., and Kandolf, R. (1992.). Ongoing enterovirus-induced myocarditis is associated with persistent heart muscle infection: quantitative analysis of virus replication, tissue damage, and inflammation. Proceedings of the National Academy of Sciences of the United States of America 89, 314-318.
Lin, T.Y., Chu, C., and Chiu, CH. (2002). Lactoferrin inhibits enterovirus 71 infection of human embryonal habdomyosarcoma cells in vitro. The Journal of infectious diseases 186, 1161-1164.
Wang, J.R., Tuan, Y.C., Tsai, H.P., Yan, J.J., Liu, CC, and Su, IJ. (2002). Change of major genotype of enterovirus 71 In outbreaks of hand-foot-and-mouth disease in Taiwan between 1998 and 2000. Journal of clinical microbiology 40, 10-15.
Shimizu, H., Utama, A., Yoshii, K., Yoshida, H., Yoneyama, T., Sinniah, M., Yusof, M.A., Okuno, Y., Okabe, N., Shih, S.R., et al. (1999). Enterovirus 71 from fatal and nonfatal cases of hand, foot and mouth disease epidemics in Malaysia, Japan and Taiwan in 1997-1998. Japanese journal of infectious diseases 52, 12-15.
Kim, H.J., Hyeon, J.Y., Hwang, S., Lee, Y.P., Lee, S.W., Yoo, U.S., Kang, B., Ahn, J.B., Jeong, Y.S., and Lee, J.W. (2016). Epidemiology and virologic investigation of human enterovirus 71 infection in the Republic of Korea from 2007 to 2012: a nationwide cross-sectional study. BMC infectious diseases 16, 425.
Wang, B., and Xiao, J.G. (2002). Effect of tetrandrine on free intracellular calcium in cultured calf basilar artery smooth muscle cells. Acta Pharmacol Sin 23, 1121-1126.
Kwan, C.Y., and Achike, F.I. (2002). Tetrandrine and related bis-benzylisoquinoline alkaloids from medicinal herbs: cardiovascular effects and mechanisms of action. Acta Pharmacol Sin 23, 1057-1068.
Kwan, C.Y., Leung, Y.M., Kwan, T.K., and Daniel, E.E. (2001). Tetrandrine inhibits Ca2+ release-activated Ca2+ channels in vascular endothelial cells. Life Sci 68, 841-847.
Wang, G., and Lemos, J.R. (1995). Tetrandrine: a new ligand to block voltage-dependent Ca 2+ and Ca(+)-activated K + channels. Life Sci 56, 295-306.
Lavecchia, A., and Di Giovanni, C. (2013). Virtual screening strategies in drug discovery: a critical review. Current medicinal chemistry 20, 2839-2860.
Stahura, F.L., and Bajorath, J. (2005). New methodologies for ligand-based virtual screening. Current pharmaceutical design 11, 1189-1202.
Tanrikulu, Y., and Schneider, G. (2008). Pseudoreceptor models in drug design: bridging ligand-and receptor-based virtual screening. Nature reviews. Drug discovery 7, 667-677.
Irwin, J.J., and Shoichet, B.K. (2005). Zinc—a free database of commercially available compounds for virtual screening. Journal of chemical information and modeling 45, 177-182.

Parhi, P., Suklabaidya, S., and Kumar Sahoo, S. (2017). Enhanced anti-metastatic and anti-tumorigenic efficacy of Berbamine loaded lipid nanoparticles in vivo. Sci Rep 7, 5806.
Liu, Q., Wang, J., Yang, L., Jia, Y., and Kong, L. (2013). A rapid and sensitive LC-MS/MS assay for the determination of berbamine in rat plasma with application to preclinical pharmacokinetic study. J Chromatogr B Analyt Technol Biomed Life Sci 929, 70-75.
Puri, A., Loomis, K., Smith, B., Lee, J.H., Yavlovich, A., Heldman, E., and Blumenthal, R. (2009). Lipid-based nanoparticles as pharmaceutical drug carriers: from concepts to clinic. Crit Rev Ther Drug Carrier Syst 26, 523-580.
De Jong, W.H., and Borm, PJ. (2008). Drug delivery and nanoparticles:applications and hazards. IntJ Nanomedicine 3, 133-149.
Lee, B.K., Yun, Y.H., and Park, K. (2015). Smart Nanoparticles for Drug Delivery: Boundaries and Opportunities. Chem Eng Sci 125, 158-164.
Dumont, C., Bourgeois, S., Fessi, H., and Jannin, V. (2018). Lipid-based nanosuspensions for oral delivery of peptides. a critical review. Int J Pharm 541, 117-135.
Adhikari, P., Pal, P., Das, A.K., Ray, S., Bhattacharjee, A, and Mazumder, B. (2017). Nano lipid-drug conjugate: An integrated review. Int J Pharm 529, 629-641.
Mohanty, C., and Sahoo, S.K. (2010). The in vitro stability and in vivo pharmacokinetics of curcumin prepared as an aqueous nanoparticulate formulation. Biomaterials 31, 6597-6611.
Miner, J.J., Cao, B., Govero, J., Smith, A.M., Fernandez, E., Cabrera, O.H., Garber, C., Noll, M,., Klein, R.S., Noguchi, K.K., et al. (2016). Zika Virus Infection during Pregnancy in Mice Causes Placental Damage and Fetal Demise. Cell 165, 1081-1091.
Zellweger, R.M., and Shresta, S. (2014). Mouse models to study dengue virus immunology and pathogenesis. Front Immunol 5, 151.
Zust, R., Toh, Y.X., Valdes, I., Cerny, D., Heinrich, J., Hermida, L., Marcos, E., Guillen, G., Kalinke, U., Shi, P.Y., et al. (2014). Type I interferon signals in macrophages and dendritic cells control dengue virus infection: implications for a hew mouse model to test dengue vaccines. J Virol 88, 7276-7285.
Zellweger, R.M., Prestwood, T.R., and Shresta, S. (2010). Enhanced infection of liver sinusoidal endothelial cells in a mouse model of antibody-induced severe dengue disease. Cell Host Microbe 7, 128-139.
Chen Y, Liu Q, Guo D. Emerging coronaviruses: Genome structure, replication, and pathogenesis. J Med Virol 2020.
Ryu S, Chun BC. Epidemiological characteristics of 2019 novel coronavirus: an interim review. Epidemiol Health 2020: e2020006.
Tortorici MA, Veesler D. Structural insights into coronavirus entry. Adv Virus Res 2019; 105: 93-116.
Shang J, Wan Y, Luo C, et al. Cell entry mechanisms of SARS-CoV-2. Proc Natl Acad Sci U S A 2020; 117(21): 11727-34.
Wang Q, Zhang Y, Wu L, et al. Structural and Functional Basis of SARS-CoV-2 Entry by Using Human ACE2. Cell 2020; 181(4): 894-904 e9.
Lukassen S, Chua RL, Trefzer T, et al. SARS-CoV-2 receptor ACE2 and TMPRSS2 are primarily expressed in bronchial transient secretory cells. EMBO J 2020; 39(10): e105114.
McAndrews KM, Kalluri R. Mechanisms associated with biogenesis of exosomes in cancer. Mol Cancer 2019; 18(1): 52.
Santoni G, Morelli MB, Amantini C, Nabissi M, Santoni M, Santoni A. Involvement of the TRPML Mucolipin Channels in Viral Infections and Anti-viral Innate Immune Responses. Front Immunol 2020; 11: 739.
Rinkenberger N, Schoggins JW. Mucolipin-2 Cation Channel Increases Trafficking Efficiency of Endocytosed Viruses. mBio 2018; 9(1).
Grimm C, Butz E, Chen CC, Wahl-Schott C, Biel M. From mucolipidosis type IV to Ebola: TRPML and two-pore channels at the crossroads of endo-lysosomal trafficking and disease. Cell Calcium 2017; 67: 148-55.
Finkelshtein D, Werman A, Novick D, Barak S, Rubinstein M. LDL receptor and its family members serve as the cellular receptors for vesicular stomatitis virus. Proceedings of the National Academy of Sciences 110, 7306-7311 (2013).

(56) References Cited

OTHER PUBLICATIONS

Raynor CM, Wright JF, Waisman DM, Pryzdial EL. Annexin II enhances cytomegalovirus binding and fusion to phospholipid membranes. Biochemistry 38, 5089-5095 (1999).
Mei M, et al. Identification of novel viral receptors with cell line expressing viral receptor-binding protein. Scientific reports 5, 7935 (2015).
Gonzalez-Reyes S, et al. Role of annexin A2 in cellular entry of rabbit vesivirus. Journal of general virology 90, 2724-2730 (2009).
Gunaratne GS, Yang Y, Li F, Walseth TF, Marchant JS. NAADP-dependent Ca(2+) signaling regulates Middle East respiratory syndrome-coronavirus pseudovirus translocation through the endolysosomal system. Cell Calcium 75, 30-41 (2018).
Grimm C, Chen CC, Wahl-Schott C, Biel M. Two-Pore Channels: Catalyzers of Endolysosomal Transport and Function. Front Pharmacol 8, 45 (2017).
Patel S. Function and dysfunction of two-pore channels. Sci Signal 8, re7 (2015).
Naylor E, et al. Identification of a chemical probe for NAADP by virtual screening. Nat Chem Biol 5, 220-226 (2009).
Abe K, Puertollano R. Role of TRP channels in the regulation of the endosomal pathway. Physiology (Bethesda) 26, 14-22 (2011).
Grimm C, Bartel K, Vollmar AM, Biel M. Endolysosomal Cation Channels and Cancer-A Link with Great Potential. Pharmaceuticals (Basel) 11, (2018).
Cheng X, Shen D, Samie M, Xu H. Mucolipins: Intracellular TRPML 1-3 channels. FEBS Lett 584, 2013-2021 (2010).
Feng X, Xiong J, Lu Y, Xia X, Zhu MX. Differential mechanisms of action of the mucolipin synthetic agonist, ML-SA1, on insect TRPML and mammalian TRPML1. Cell Calcium 56, 446-456 (2014).
Zeevi DA, Frumkin A, Bach G. TRPML and lysosomal function. Biochimica et Biophysica Acta (BBA)—Molecular Basis of Disease 1772, 851-858 (2007).
Bach G. Mucolipin 1: endocytosis and cation channel—a review. Pflugers Archiv 451, 313-317 (2005).
Sun M, et al. Mucolipidosis type IV is caused by mutations in a gene encoding a novel transient receptor potential channel. Human molecular genetics 9, 2471-2478 (2000).
Berman E, Livni N, Shapira E, Merin S, Levij I. Congenital corneal clouding with abnormal systemic storage bodies: a new variant of mucolipidosis. The Journal of pediatrics 84, 519-526 (1974).
Bargal R, et al. Identification of the gene causing mucolipidosis type IV. Nature genetics 26, 118-122 (2000).
Go GW, Mani A. Low-density lipoprotein receptor (LDLR) family orchestrates cholesterol homeostasis. Yale J Biol Med 85, 19-28 (2012).
Chu H, et al. Comparative replication and immune activation profiles of SARS-CoV-2 and SARS-CoV in human lungs: an ex vivo study with implications for the pathogenesis of COVID-19. Clin Infect Dis, (2020).
Wei J-c, et al. Design and evaluation of a multi-epitope peptide against Japanese encephalitis virus infection in BALB/c mice. Biochemical and biophysical research communications 396, 787-792 (2010).
Miao Y, Li G, Zhang X, Xu H, Abraham SN. A TRP Channel Senses Lysosome Neutralization by Pathogens to Trigger Their Expulsion. Cell 2015; 161(6): 1306-19.
Schoggins JW, Wilson SJ, Panis M, et al. A diverse range of gene products are effectors of the type I interferon antiviral response. Nature 2011; 472(7344): 481-5.
Zhou P, Yang XL, Wang XG, et al. A pneumonia outbreak associated with a new coronavirus of probable bat origin. Nature 2020; 579(7798): 270-3.
Lan J, Ge J, Yu J, et al. Structure of the SARS-CoV-2 spike receptor-binding domain bound to the ACE2 receptor. Nature 2020; 581(7807): 215-20.
Chen X, Cao R, Zhong W. Host Calcium Channels and Pumps in Viral Infections. Cells 2019; 9(1).
Gu Y, Zhang J, Ma X, et al. Stabilization of the c-Myc Protein by CAMKIIgamma Promotes T Cell Lymphoma. Cancer Cell 2017; 32(1): 115-28 e7.
Gu Y, Chen T, Meng Z, et al. CaMKII gamma, a critical regulator of CML stem/progenitor cells, is a target of the natural product berbamine. Blood 2012; 120(24): 4829-39.
Zhang CM, Gao L, Zheng YJ, Yang HT. Berbamine protects the heart from ischemia/reperfusion injury by maintaining cytosolic Ca(2+) homeostasis and preventing calpain activation. Circ J 2012; 76(8): 1993-2002.
Xu YH, Liu J, Zhang SP, Liu LH. The effect of berbamine derivatives on activated Ca2+-stimulated Mg2+-dependent ATPase in erythrocyte membranes. Biochem J 1987; 248(3): 985-8.
Li BY, Zhang YC, Li WH. Effects of berbamine on contraction and Ca2+ influx of pig basilar artery. Zhongguo Yao Li Xue Bao 1992; 13(5): 412-6.
Ortega FG, Roefs MT, de Miguel Perez D, et al. Interfering with endolysosomal trafficking enhances release of bioactive exosomes. Nanomedicine 2019; 20: 102014.
Chang-Xiao Liu PGX, Guo-Sheng Liu. Studies on plant resources, pharmacology and clinical treatment with perbamine. Phytotherapy Research 1991; 5(5): 228-30.
Kumazawa Y, Kaneko M, Inagaki K, Matsuzaki N, Nomoto K. Accelerated recovery from gamma-irradiation-induced leukopenia in mice by the biscoclaurine alkaloid, Cepharanthin-comparison with recombinant human granulocyte colony-stimulating factor. Int J Immunopharmacol 1990; 12(5): 523-30.
Li SY, Jei W, Seow WK, Thong YH. Effect of berbamine on blood and bone-marrow stem cells of cyclophosphamide-treated mice. Int J Immunopharmacol 1994; 16(3): 245-9.
Mori M, Kawasaki, S., Sacho, M., Awai, M., Sadahira, Y. & Ono, M. Effect of cepharanthin on the hemopoietic suppression by X-ray irradiation—hematological studies (in Japanese). . Gann to Kagakuryouhou, 1989; 49: 667-74.
Oyaizu H, Adachi Y, Yasumizu R, et al. Protection of T cells from radiation-induced apoptosis by Cepharanthin. Int Immunopharmacol 2001; 1(12): 2091-9.
Li SY, Ling LH, Teh BS, Seow WK, Thong YH. Anti-inflammatory and immunosuppressive properties of the bis-benzylisoquinolines: in vitro comparisons of tetrandrine and berbamine. Int J Immunopharmacol 1989; 11(4): 395-401.
Ren Y, Lu L, Guo TB, et al. Novel immunomodulatory properties of berbamine through selective down-regulation of STAT4 and action of IFN-gamma in experimental autoimmune encephalomyelitis. J Immunol 2008; 181(2): 1491-8.
Kupeli E, Kosar M, Yesilada E, Husnu K, Baser C. A comparative study on the anti-inflammatory, antinociceptive and antipyretic effects of isoquinoline alkaloids from the roots of Turkish *Berberis* species. Life Sci 2002; 72(6): 645-57.
Seow WK, Ferrante A, Summors A, Thong YH. Comparative effects of tetrandrine and berbamine on production of the Inflammatory cytokines interleukin-1 and tumor necrosis factor. Life Sci 1992; 50(8): PL53-8.
Guo ZB, Fu JG. [Progress of cardiovascular pharmacologic study on berbamine]. Zhongguo Zhong Xi Yi Jie He Za Zhi 2005; 25(8): 765-8.
Zheng Y, Gu S, Li X, et al. Berbamine postconditioning protects the heart from ischemia/reperfusion injury through modulation of autophagy. Cell Death Dis 2017; 8(2): e2577.
Hu H, Zhou S, Sun X, et al. A potent antiarrhythmic drug N-methyl berbamine extends the action potential through Inhibiting both calcium and potassium currents. J Pharmacol Sci 2020; 142(4): 131-9.
Li BY, Qiao GF, Zhao YL, Zhou H, Li WH. Effects of berbamine on ATP-induced [Ca2+]i mobilization in cultured vascular smooth muscle cells and cardiomyocytes. Zhongguo Yao Li Xue Bao 1999; 20(8): 705-8.
Qiao GF, Zhou H, Li BY, Li WH. Antagonistic effects of berbamine on [Ca2+]i mobilization by KCl, norepinephrine, and caffeine in newborn rat cardiomyocytes. Zhongguo Yao Li Xue Bao 1999; 20(4): 292-6.
Leung YM, Berdik M, Kwan CY, Loh TT. Effects of tetrandrine and closely related bis-benzylisoquinoline derivatives on cytosolic Ca2+

(56) References Cited

OTHER PUBLICATIONS in human leukaemic HL-60 cells: a structure-activity relationship study. Clin Exp Pharmacol Physiol 1996; 23(8): 653-9.

Li Z, Mbah NE, Maltese WA. Vacuole-inducing compounds that disrupt endolysosomal trafficking stimulate production of exosomes by glioblastoma cells. Mol Cell Biochem 2018; 439(1-2): 1-9.

Palmulli R, van Niel G. To be or not to be . . . secreted as exosomes, a balance finely tuned by the mechanisms of biogenesis. Essays Biochem 2018; 62(2): 177-91.

Mou L, Liang B, Liu G, et al. Berbamine exerts anticancer effects on human colon cancer cells via induction of autophagy and apoptosis, inhibition of cell migration and MEK/ERK signalling pathway. J Buon 2019; 24(5): 1870-5.

Kapoor S. Emerging role of berbamine as an anti-cancer agent in systemic malignancies besides chronic myeloid eukemia. J Zhejiang Univ Sci B 2012; 13(9): 761-2; author reply 2.

Hou ZB, Lu KJ, Wu XL, Chen C, Huang XE, Yin HT. In vitro and in vivo antitumor evaluation of berbamine for lung cancer treatment. Asian Pac J Cancer Prev 2014; 15(4): 1767-9.

Meng Z, Li T, Ma X, et al. Berbamine inhibits the growth of liver cancer cells and cancer-initiating cells by targeting Ca (2)(+)/calmodulin-dependent protein kinase II. Mol Cancer Ther 2013; 12(10): 2067-77.

Zhang H, Jiao Y, Shi C, et al. Berbamine suppresses cell viability and induces apoptosis in colorectal cancer via activating p53-dependent apoptotic signaling pathway. Cytotechnology 2018; 70(1): 321-9.

Liang Y, He X, Li X, et al. 4-Chlorbenzoyl Berbamine, a Novel Derivative of the Natural Product Berbamine, Potently Inhibits the Growth of Human Myeloma Cells by Modulating the NF-kappaB and JNK Signalling Pathways. Cancer Invest 2016; 34(10): 496-505.

Yang F, Nam S, Zhao R, et al. A novel synthetic derivative of the natural product berbamine inhibits cell viability and Induces apoptosis of human osteosarcoma cells, associated with activation of JNK/AP-1 signaling. Cancer Biol Ther 2013; 14(11): 1024-31.

Nam S, Xie J, Perkins A, et al. Novel synthetic derivatives of the natural product berbamine inhibit Jak2/Stat3 signaling and induce apoptosis of human melanoma cells. Mol Oncol 2012; 6(5): 484-93.

Zhang H, Jiao Y, Shi C, et al. Berbamine suppresses cell proliferation and promotes apoptosis in ovarian cancer partially via the inhibition of Wnt/beta-catenin signaling. Acta Biochim Biophys Sin (Shanghai) 2018; 50(6): 532-9.

Chen WC, Simanjuntak Y, Chu LW, et al. Benzenesulfonamide Derivatives as Calcium/Calmodulin-Dependent Protein Kinase Inhibitors and Antiviral Agents against Dengue and Zika Virus Infections. J Med Chem 2020; 63(3): 1313-27.

Stefanovic S, Windsor M, Nagata KI, Inagaki M, Wileman T. Vimentin rearrangement during African swine fever virus Infection involves retrograde transport along microtubules and phosphorylation of vimentin by calcium calmodulin kinase Ii. J Virol 2005; 79(18): 11766-75.

De Oliveira DE, Ballon G, Cesarman E. NF-kappaB signaling modulation by EBV and KSHV. Trends Microbiol 2010; 18(6): 248-57.

Seif F, Aazami H, Khoshmirsafa M, et al. JAK Inhibition as a New Treatment Strategy for Patients with COVID-19. Int Arch Allergy Immunol 2020; 181(6): 467-75.

Huang P, Xu M, Wu Y, Rizvi Syeda AK, Dong XP. Multiple facets of TRPML1 in autophagy. Cell Calcium 2020; 88: 102196.

Ahmad L, Mostowy S, Sancho-Shimizu V. Autophagy—Virus Interplay: From Cell Biology to Human Disease. Front Cell Dev Biol 2018; 6: 155.

Bello-Perez M, Sola I, Novoa B, Klionsky DJ, Falco A. Canonical and Noncanonical Autophagy as Potential Targets for COVID-19. Cells 2020; 9(7).

Bhatt S, et al. The global distribution and burden of dengue. Nature 496, 504 (2013).

Daep CA, Muñoz-Jordan JL, Eugenin EA. Flaviviruses, an expanding threat in public health: focus on dengue, West Nile, and Japanese encephalitis virus. Journal of neurovirology 20, 539-560 (2014).

Ghosh D, Basu A. Present perspectives on flaviviral chemotherapy. Drug discovery today 13, 619-624 (2008).

Kok WM. New developments in flavivirus drug discovery. Expert opinion on drug discovery 11, 433-445 (2016).

Lee M-S, Tseng F-C, Wang J-R, Chi C-Y, Chong P, Su I-J. Challenges to licensure of enterovirus 71 vaccines. PLoS neglected tropical diseases 6, (2012).

* cited by examiner

| Antibody or Reagent | Vendor | Catalog No. | Species | Application | Dilution |
|---|---|---|---|---|---|
| ACE2 | Abcam | ab15348 | Rabbit | Flow cytometry, immunofluorescence staining | 1:200 |
| DPP4 | Abcam | ab119346 | Mouse | Flow cytometry, immunofluorescence staining | 1:50 |
| LAMP1 | Cell Signalling | 9091 | Rabbit | Immunofluorescence staining | 1:200 |
| SARS-CoV-2 NP | - | - | Rabbit | Immunofluorescence staining | 1:2000 |
| Wheat Germ Agglutinin-488 | Invitrogen | W6748 | - | Immunofluorescence staining | 1:500 |
| Hochest | Invitrogen | H3569 | - | Immunofluorescence staining | 1:1000 |
| Propidium Iodide | Invitrogen | P3566 | - | Immunofluorescence staining | 1:1000 |
| DAPI | Invitrogen | 62247 | - | Immunofluorescence staining | 1µg/mL |
| HSP 70 | Santa Cruz | sc-24 | Mouse | Western Blotting | 1:500 |
| TSG101 | Proteintech | 14497-1-AP | Rabbit | Western Blotting | 1:500 |
| CD63 | Proteintech | 25682-1-AP | Rabbit | Western Blotting | 1:500 |
| Alix | Proteintech | 12422-1-AP | Rabbit | Western Blotting | 1:500 |
| ACE2 | Proteintech | 21115-1-AP | Rabbit | Western Blotting | 1:500 |

Fig. 16

USE OF BERBAMINE OR ITS ANALOGUE FOR PREVENTING OR TREATING RNA VIRUS INFECTION

CROSS REFERENCE TO RELATED APPLICATIONS

This application is a 371 National Phase filing of International PCT Application No. PCT/CN2020/113378 filed Sep. 4, 2020, which claims priority to and is a continuation-in-part of U.S. Non-Provisional application Ser. No. 16/559,869 filed Sep. 4, 2019, and which also claims the benefit of U.S. Provisional Application No. 63/026,350 filed May 18, 2020, the disclosures of which are hereby incorporated by reference.

TECHNICAL FIELD

The present invention relates to a method of preventing or treating a subject suffering from an infection caused by a RNA virus including infections caused by a positive single-stranded RNA virus. The method is useful in prevention or treatment of an infection caused by a flavivirus, an enterovirus, a lentivirus or a coronavirus infection.

BACKGROUND OF THE INVENTION

RNA viruses, particularly positive single-stranded RNA viruses, such as viruses from Flaviviridae, Enterovirus and Coronavirus are expanding huge threat in public health. West Nile virus, Japanese encephalitis virus (JEV), Zika virus (ZIKV), Dengue virus (DENV), and enterovirus A17 (EV-A17) are considered as the leading causes of human and animal infectious diseases in the world. The morbidity and mortality of related illness caused by these viruses have been increasing every year. West Nile virus has recently spread from the Mediterranean Basin to the Western Hemisphere and now accounts for thousands of sporadic encephalitis cases each year. Also, Japanese encephalitis have caused thousands of deaths each year in a wide range of endemic areas.

Although there are some commercially available vaccines against yellow fever, Japanese encephalitis and neonatal encephalitis, there are few or almost no effective clinical treatment against flaviviruses or enteroviruses. For example, patients suffering from serious flavivirus or enterovirus infection may only receive supportive care including administration with intravenous fluids, hospitalization, respiratory support, and prevention of secondary infections. There is currently a lack of effective remedy in treating RNA virus infection particularly caused by flaviviruses and enteroviruses.

Furthermore, a coronavirus is a kind of RNA virus that causes mild to moderate respiratory illness. Whilst most of the coronaviruses are not dangerous, with some only have mild symptoms, certain coronaviruses such as Middle East Reparatory Syndrome (MERS-CoV), Severe Acute Respiratory Syndrome (SARS-CoV), Severe Acute Respiratory Syndrome Coronavirus 2 (SARS-CoV-2) are serious types which trigger severe symptoms. The spread of the illness can be uncontrollable. Currently, COVID-19 infections caused by SARS-CoV-2 has already reached over 24 million globally and the number of deaths increases every day. The COVID-19 pandemic also causes worldwide lockdown, causing significant economic losses worldwide.

Accordingly, there remains an urgent need for therapy, and/or novel compounds which are useful in the prevention or treatment of RNA viral infection particularly flavivirus infection and coronavirus infection.

SUMMARY OF THE INVENTION

In an aspect, the present invention pertains to a method of preventing or treating a subject suffering from a flavivirus infection by administering an effective amount of berbamine or its analogue to the subject, berbamine has a structure of Formula (I):

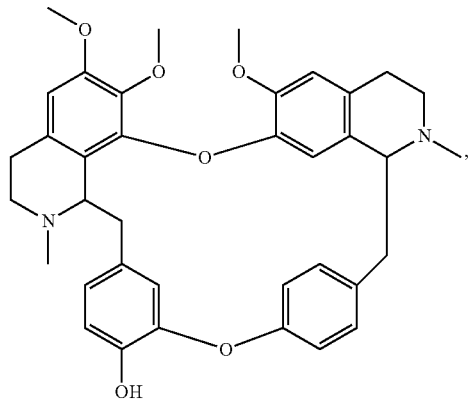

Formula (I)

wherein the flavivirus infection is caused by Japanese encephalitis virus, Zika virus or Dengue virus.

In another aspect, the present invention pertains to a method of inhibiting the entry of a flavivirus into host cells, comprising contacting the host cells with an effective amount of berbamine or its analogue, berbamine has a structure of Formula (I):

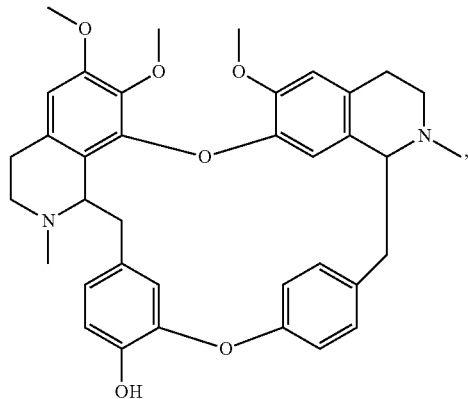

Formula (I)

wherein the flavivirus is Japanese encephalitis virus, Zika virus or Dengue virus.

In a further aspect, the present invention relates to a method of inhibiting the entry of an enterovirus and/or a lentivirus into host cells, comprising contacting the host cells with an effective amount of berbamine or its analogue as described above.

Still further, the present invention relates to use of berbamine or its analogue in prevention or treatment of a RNA virus infection, particularly but not exclusively a flavivirus infection, an enterovirus infection or a lentivirus infection.

Furthermore, the present invention also pertains to use of berbamine or its analogue in the preparation of a medicament for preventing or treating a RNA virus infection, particularly but not exclusively a flavivirus infection, an enterovirus infection or a lentivirus infection.

In one aspect, the present invention also pertains to a method of preventing or treating a subject suffering from a coronavirus infection, particularly infection caused by MERS-CoV and/or SARS-CoV-2, by administering an effective amount of berbamine or its analogue to the subject. It would be appreciated that the invention also relates to a method of inhibiting the entry of a coronavirus into host cells.

There is also provided use of berbamine or its analogue in the preparation of a medication for preventing or treating a coronavirus infection.

The inventors unexpectedly found that benzylisoquinoline alkaloids of the present invention, i.e. berbamine and its analogues, have an antiviral effect, particularly against RNA virus infections such as a flavivirus infection, an enterovirus infection, a lentivirus infection, and a coronavirus infection. The inventors found that berbamine and its analogues are capable of inhibiting the entry of the viruses into host cells thereby protecting the cells from being infected. Mice infected with the virus particularly flavivirus were also found to have higher survival rate after treatment with the benzylisoquinoline alkaloids. There are also experimental data indicating that berbamine is effective in inhibiting the entry of MERS-CoV and SARS-CoV-2 into host cells. Accordingly, the present invention provides effective compounds for treating and/or preventing flavivirus infection, particularly Japanese encephalitis virus infection, Zika virus infection and/or Dengue virus infection, as well as coronavirus infection.

Those skilled in the art will appreciate that the invention described herein is susceptible to variations and modifications other than those specifically described. The invention includes all such variations and modifications. The invention also includes all steps and features referred to or indicated in the specification, individually or collectively, and any and all combinations of the steps or features.

Other features and aspects of the invention will become apparent by consideration of the following detailed description and accompanying drawings.

BRIEF DESCRIPTION OF THE DRAWINGS

FIG. 16 shows a table summarizing the antibodies and reagents used in flow cytometric analysis, immunofluorescence staining, and Western Blot analysis.

DETAILED DESCRIPTION OF THE INVENTION

Figure 1A:
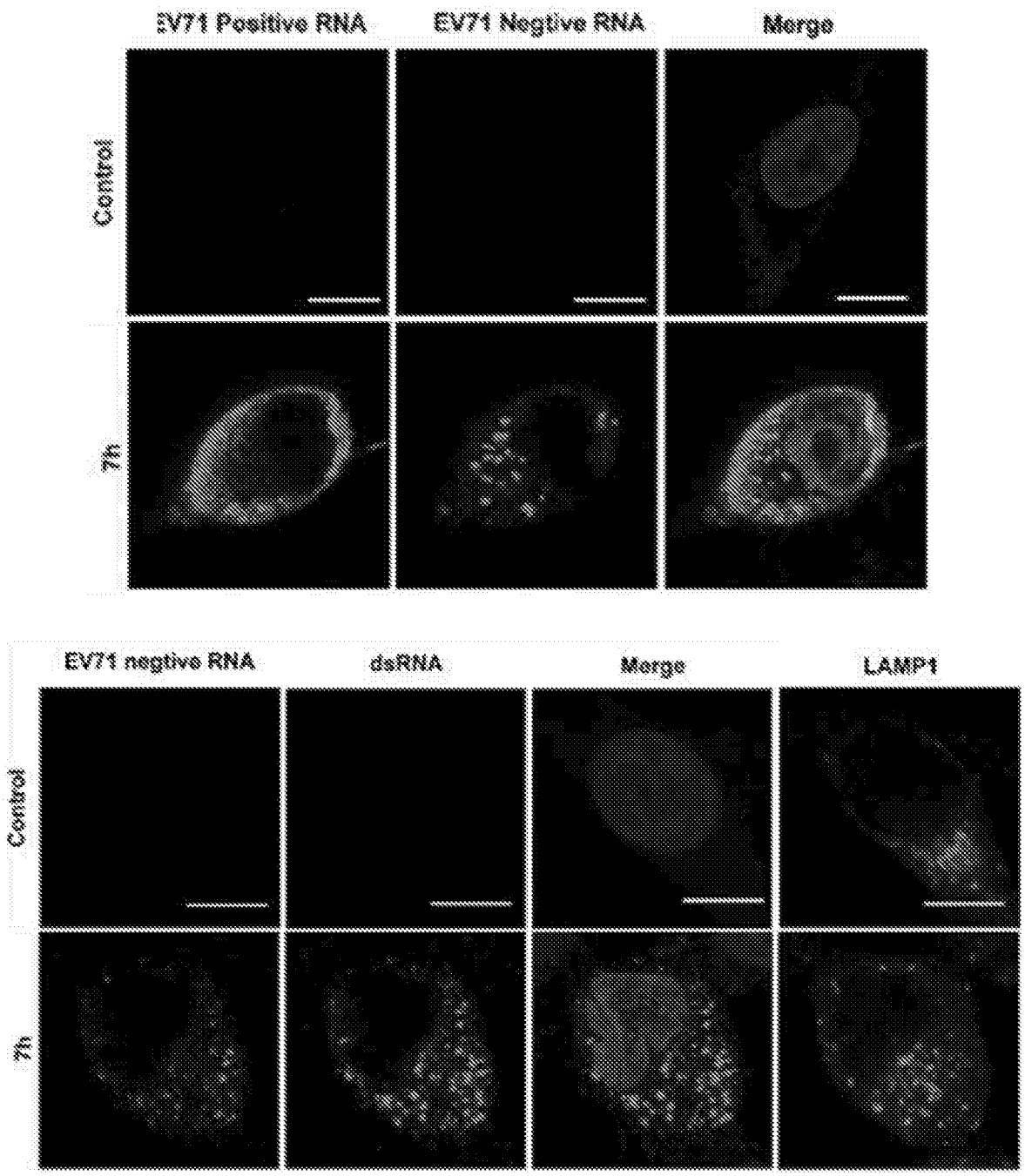
FIG. 1A shows the microscopic images of HeLa cells obtained after in situ hybridization of EV-71 positive strand RNA and EV71 negative strand RNA and immunostaining of dsRNA or LAMP1, in which the HeLa cells were infected with EV-71 (MOI=1) for 7 h and EV-71 virions were observed.

Unless otherwise defined, all technical terms used herein have the same meaning as commonly understood by one skilled in the art to which the invention belongs.

As used herein, "comprising" means including the following elements but not excluding others.

"Essentially consisting of" means that the material consists of the respective element along with usually and unavoidable impurities such as side products and components usually resulting from the respective preparation or method for obtaining the material such as traces of further components or solvents. "Consisting of" means that the material solely consists of, i.e. is formed by the respective element. As used herein, the forms "a", "an", and "the" are intended to include the singular and plural forms unless the context clearly indicates otherwise.

The present invention in an aspect provides a method of preventing or treating a subject suffering from a RNA virus infection particularly an infection caused by a positive single-stranded RNA virus. The RNA virus may be a flavivirus, an enterovirus, a lentivirus, or a coronavirus.

In embodiments herein, the method is suitable for preventing or treating a subject suffering from a flavivirus infection by administering an effective amount of berbamine or its analogue to the subject.

In an embodiment, the flavivirus is Japanese encephalitis virus, Zika virus or Dengue virus. In an alternative embodiment, the flavivirus may be selected from the group consisting of West Nile virus, Murray Valley encephalitis virus, and Yellow Fever virus.

Berbamine and its analogue can be classified as bisbenzylisoquinoline alkaloids including two benzylisoquinoline moieties linked through diphenyl ether, benzyl phenyl ether or biphenyl bonds. Berbamine and its analogue may be artificially synthesized or may be a naturally occurring compound derived from a plant material, a fungus or the like.

Berbamine has a structure of Formula (I)

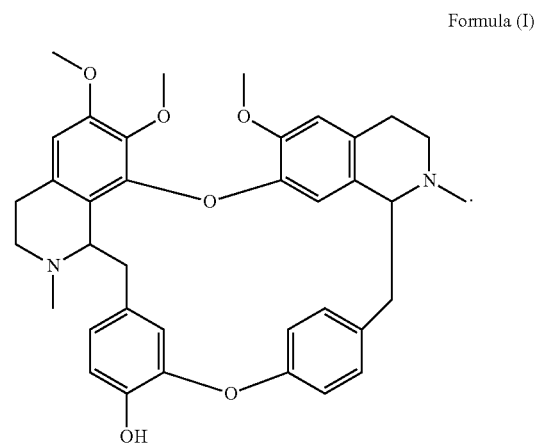 [SMILES: COc1cc2c3cc1Oc1c(OC)c(OC)cc4c1C(Cc1ccc(O)c(c1)Oc1ccc(cc1)CC3N(C)CC2)N(C)CC4]

Formula (I)

Analogues of berbamine generally share a core structure of Formula (Ib):

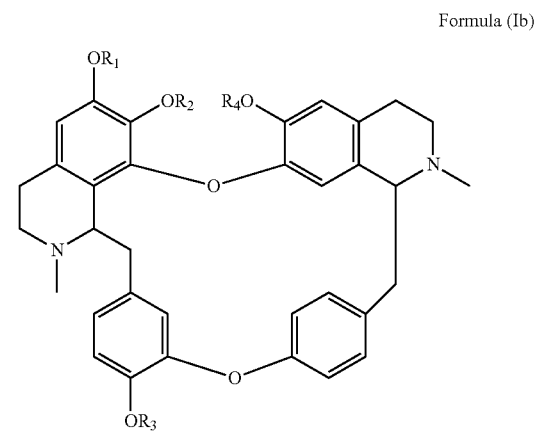

Formula (Ib)

wherein $R_1$, $R_2$, $R_3$, $R_4$ are independently selected from a hydrogen atom, a C1-C3 alkyl group, a halogen atom or a nitrogen containing group, and with the provision that the analogue is not tetrandrine. C1-C3 alkyl group may be any of a methyl group, an ethyl group, a propyl group, an isopropyl group, or a cyclopropyl group. The halogen atom may be selected from the group consisting of fluorine, chlorine, and bromine.

In an embodiment, the analogue of berbamine preferably has a structure of Formula (II), (III), or (IV):

Formula (II)

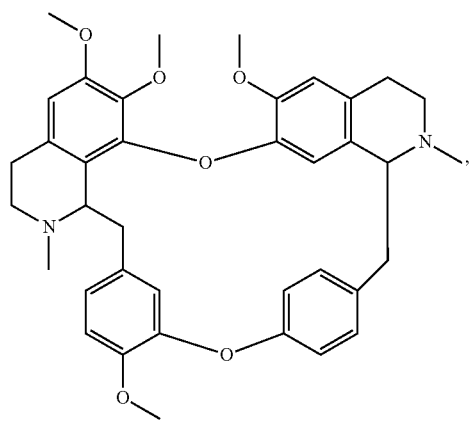

Formula (III)

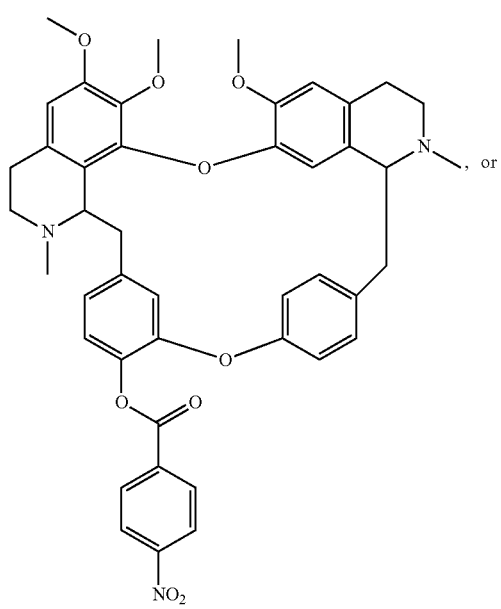, or

Formula (IV)

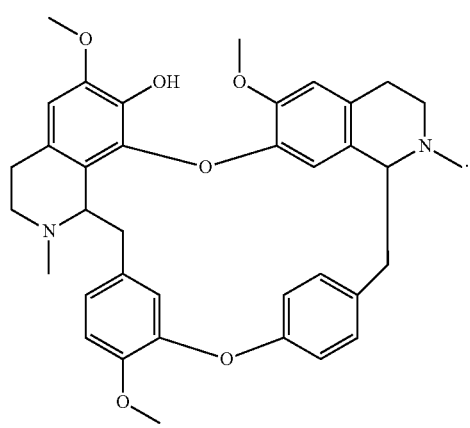.

In an embodiment, the analogue of berbamine has a structure of Formula (IIb), (IIIb), or (IVb):

Formula (IIb)

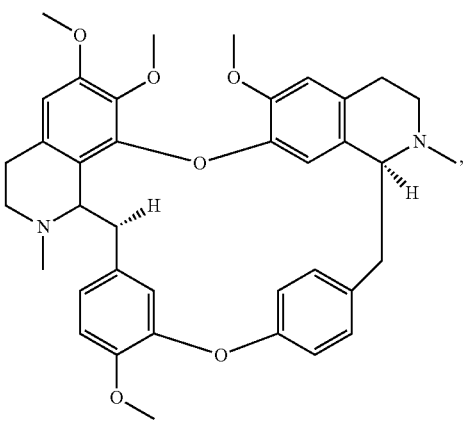,

Formula (IIIb)

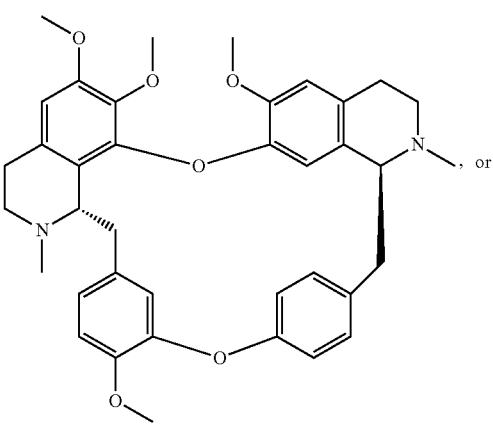, or

Formula (IVb)

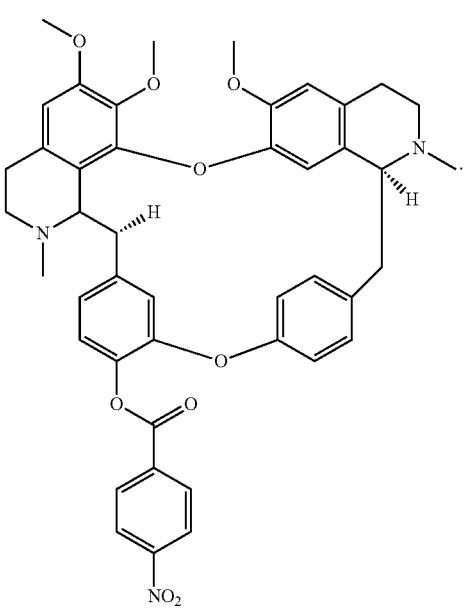.

The inventors found that berbamine and its analogues as disclosed above are effective against flavivirus for example by inhibiting the entry of the virus into the host cells, and/or protecting a subject from being infected at a particular dose. They are potential anti-viral agents particularly anti-flavivirus agents.

Berbamine is found to be exceptionally suitable for use in prevention and treatment of flavivirus infection. The inventors proved that berbamine has an inhibitory effect against at least JEV, ZIKV, DENV-2, EV-71 and lentivirus.

Berbamine and its analogues as disclosed herein may also inhibit the entry of an enterovirus and/or a lentivirus into host cells of the subject, thereby boosting the immunity of the subject against various types of virus. The inventors also found that their antiviral effects are not cell-specific.

It would be appreciated that salts or solvates of berbamine and its analogues are also included in the scope, and may be used for preventing or treating the same virus infection.

The method of the present invention may be used as a precautionary method to prevent a subject from suffering a RNA virus infection, e.g. a flavivirus infection, as the method is useful in boosting the immune system in an individual, inhibiting the entry of the virus into host cells, and/or inhibiting the interaction between the virus and the host cells. The method can also delay the onset or slow down the progression of a condition associated with the infection in an individual. It would be appreciated that the treatment of the infection may involve inhibition of the viral proteins in the infected subject, killing of the virus, alleviating symptoms caused by the virus, and/or inhibiting the synthesis of the virus, or the combinations thereof.

The term "subject" in particular refers to an animal or human, in particular a mammal and most preferably human. In an embodiment, the subject is susceptible to a flavivirus infection, or is suffering from a flavivirus infection. In a further embodiment, the subject is suffering from two different types of RNA virus infections. In an example embodiment, the subject is susceptible to or suffering from an enterovirus infection, lentivirus infection or a combination thereof.

The expression "effective amount" generally denotes an amount sufficient to produce therapeutically desirable results, wherein the exact nature of the result varies depending on the specific condition which is treated. Berbamine or its analogue may be contained in a composition, in particular a pharmaceutical composition, in an effective amount, i.e. an amount suitable to treat or prevent the RNA virus infection particularly flavivirus infection, enterovirus infection, lentivirus infection, or coronavirus infection in a subject, in particular a mammal, which also depends on the frequency and number of compositions to be administered. In an embodiment, the subject is a mammal and berbamine or its analogue may be administered to the subject at a dose of about 15 mg/kg, about 20 mg/kg, about 25 mg/kg, about 30 mg/kg, about 35 mg/kg, about 40 mg/kg, about 45 mg/kg, about 50 mg/kg; or at a dose of about 15 mg/kg to about 50 mg/kg, about 20 mg/kg to about 50 mg/kg, or above. In other embodiment, the subject is human and berbamine or its analogue may be administered to the subject at a dose of about 15 mg/kg to about 50 mg/kg, or above.

When berbamine or its analogue is provided in a pharmaceutical composition to a subject, the skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition. Berbamine or its analogue may be formulated in a liquid form such as an aqueous solution and a non-aqueous mixture; a semi-solid form such as a gel, an emulsion, a cream and a paste; or a solid form such as a tablet, a capsule and powders. Berbamine or its analogue may also be formulated in the form of a prodrug so as to achieve the desired effect after administration.

In embodiments of the present invention, berbamine or its analogue as disclosed herein is administered to the subject by a route selected from a group consisting of oral delivery, intravenous delivery, intradermal delivery, intraperitoneal delivery and intramuscular delivery. The person skilled in the art is able to formulate berbamine or its analogue in a pharmaceutical composition according to the specific flavivirus infection and the disclosure herein.

In addition, berbamine or its analogue may be administered in combination with a compound selected from the group consisting of the following compounds and a derivative thereof:

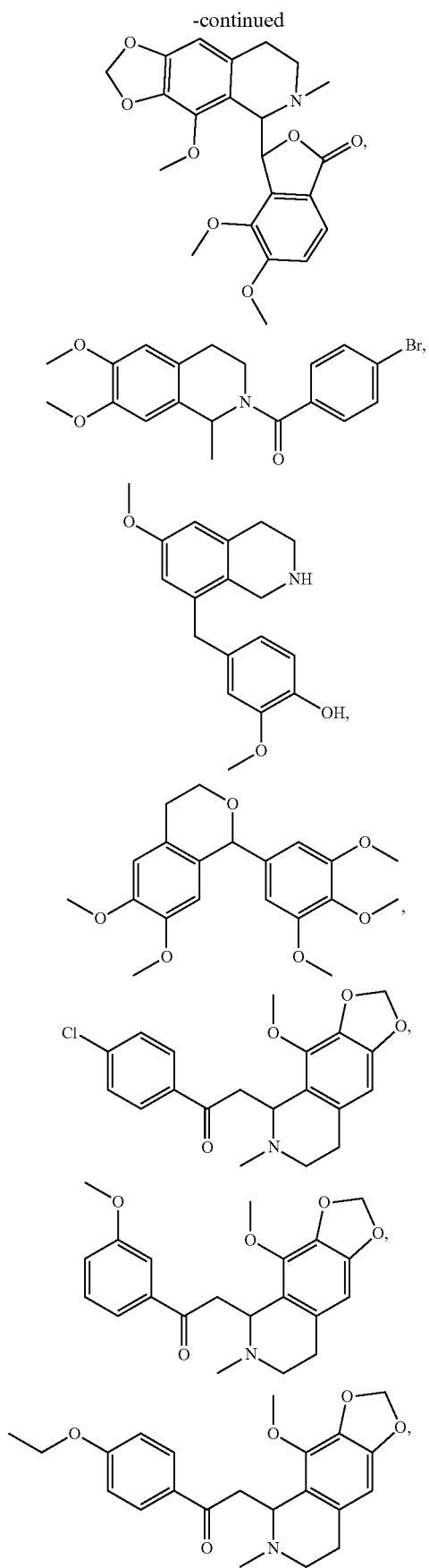

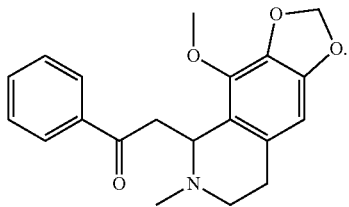

The above compounds were identified and considered to have a similar 3D conformation with berbamine. Particularly, these compounds were identified using berbamine as reference and therefore it is believed that they can achieve similar or identical inhibitory effect as berbamine. It has also been determined that the above compounds have anti-viral effect, which is described in the examples and the effect is also represented in the corresponding FIGS. 8A and 8B. The above compounds can be provided in any salt form suitable for administration or use.

It would be appreciated that the above compounds may be used alone for treating or preventing RNA virus infection such as flavivirus infection as they demonstrated antiviral effect particularly by inhibiting the entry of flavivirus into host cells. Therefore, the present invention also pertains to a method of preventing or treating a subject suffering from a flavivirus infection by administering the subject with an effective amount of a compound selected from the group consisting of the following compounds and a derivative thereof:

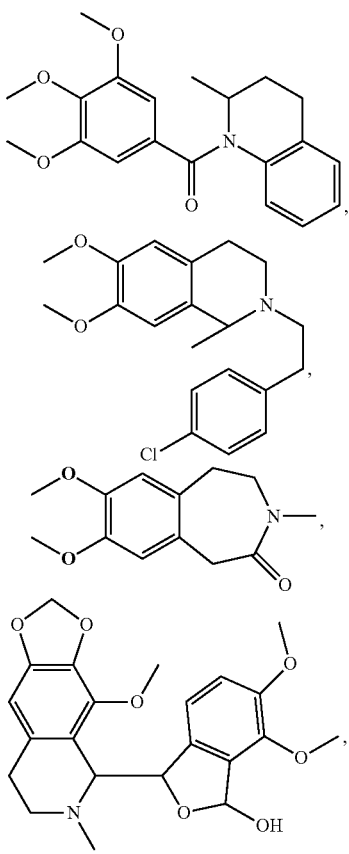

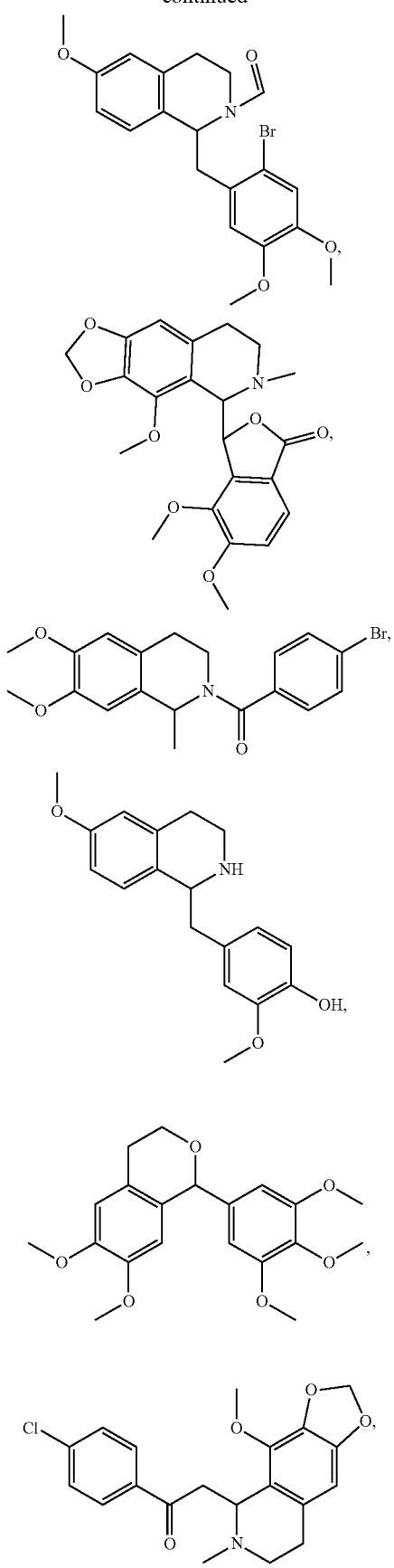

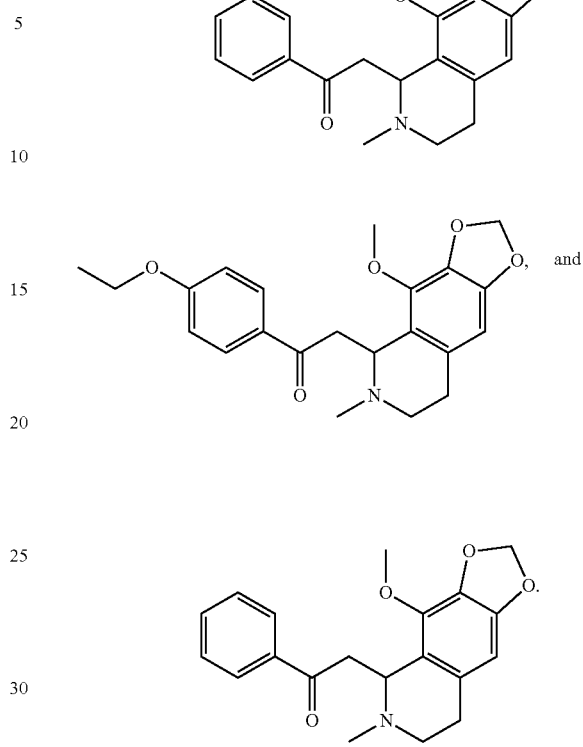

These compounds may be used to prepare a medicament for preventing or treating the infection as described above.

The present invention further pertains to a method of inhibiting the entry of a flavivirus, particularly Japanese encephalitis virus, Zika virus or Dengue virus, into host cells, comprising contacting the host cells with an effective amount of berbamine or its analogue. The flavivirus is as described above. Particularly, the flavivirus is Japanese encephalitis virus or Zika virus. Berbamine and its analogue are also as described above.

The method may comprise a step of incubating the host cells with a medium containing berbamine or its analogue for a period of time such as for at least 0.5 h, at least 1 h, at least 1.5 h, or above.

In an embodiment, berbamine or its analogue may further inhibit the entry of an enterovirus and/or a lentivirus into the host cells. Accordingly, the present invention may further relate to a method of inhibiting the entry of an enterovirus and/or a lentivirus into host cells, comprising contacting the host cells with an effective amount of berbamine or its analogue as described above. The enterovirus may be EV-A71 (also known as EV-71), and the lentivirus may encode histone B-RFP.

The inventors further found that berbamine as described above is suitable for preventing or treating a coronavirus infection, and preventing the entry of a coronavirus into host cells. Accordingly, the present invention further pertains to a method for preventing or treating a subject suffering from a coronavirus infection. The method comprises the step of administering an effective amount of berbamine or its analogue, preferably berbamine, to the subject. Berbamine and its analogue are as described above.

In particular, the coronavirus infection is caused by Middle East respiratory syndrome coronavirus (MERS- CoV) and/or severe acute respiratory syndrome coronavirus 2 (SARS-CoV-2). The inventors found that berbamine is a potential TRPMLs inhibitor that can inhibit lysosomal calcium channel. The modulation of the calcium channel via TRPML by berbamine may compromise the trafficking of ACE2, thereby preventing the entry of the coronavirus. Berbamine is also found to be able to decrease the level of DPP4 at the plasma membrane. Based on the experimental results, berbamine is found to have potential values in coronavirus therapy and prevention.

It would be appreciated that the method may be used as a precautionary method to prevent a subject from suffering a coronavirus infection, or used in a therapy, as similar to the method for preventing or treating a flavivirus infection mentioned above. In particular, berbamine may act as a TRPMLs inhibitor to inhibit the entry of the coronavirus into host cells, and improve the immune system of the subject. The method can also delay the onset or slow down the progression of a condition associated with the infection in an individual. It would be appreciated that the treatment of coronavirus infection may involve inhibition of the viral proteins in the infected subject, killing of the virus, alleviating symptoms caused by the virus, and/or inhibiting the synthesis of the virus, or the combinations thereof.

The method is suitable for a subject, particularly an animal or human as described above. In an embodiment, the subject is susceptible to a coronavirus infection, or is suffering from a coronavirus infection. For example, the subject is an individual who is about to visit a high-risk area or an elderly people who is vulnerable to the coronavirus infection. Berbamine or its analogue, particularly berbamine is provided to the subject at the effective amount, or an amount that helps boost the immune system of the subject, and in the appropriate pharmaceutical composition or form, to produce the desired therapeutic effect.

In a particular embodiment, the subject is a mammal and the berbamine or its analogue is administered to the subject at a dose of about 15 mg/kg to about 50 mg/kg, or about 20 mg/kg to about 50 mg/kg.

In embodiments therein, there is also provided a method of inhibiting the entry of a coronavirus, particularly MERS-CoV and/or SARS-CoV-2, into host cells comprising contacting the host cells with an effective amount of berbamine or its analogue, particularly berbamine is as described above.

It would be appreciated that the present invention relates to use of berbamine or its analogue in prevention or treatment of a RNA virus infection as described above, and use in the preparation of a medicament or a composition for preventing or treating of a RNA virus infection as described above. A person having ordinary skills in the art would appreciate suitable methods to prepare a medicament for the intended purposes based on the disclosure herein. In embodiments, there are also provided use of berbamine or its analogue in the preparation of a medicament for inhibiting the entry of a RNA virus, particularly a flavivirus, an enterovirus, a lentivirus, and/or a coronavirus into host cells. The medicament is capable of inhibiting the entry of the aforesaid viruses.

EXAMPLES

Figure 1B:
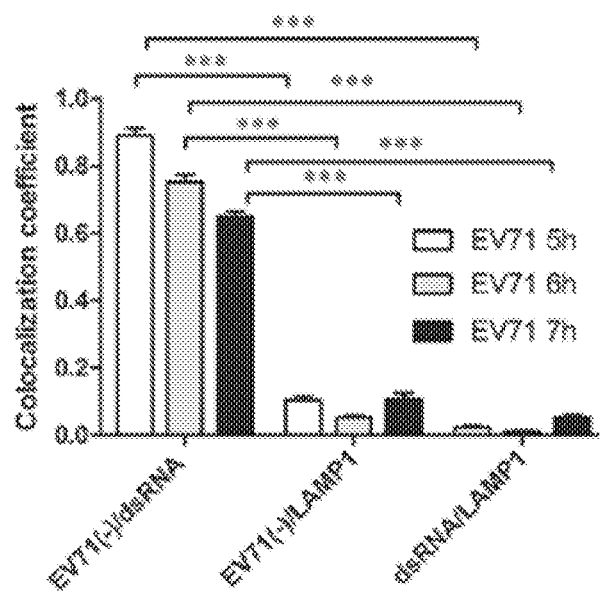
FIG. 1B is a plot prepared based on the results in FIG. 1A, demonstrating the colocalization coefficient of the EV-71 positive strand RNA and EV71 negative strand RNA in the infected cells.

I. Determination of Anti-Viral Effect of Berbamine Against Flavivirus, Enterovirus, and Lentivirus Assay for Detecting Viral Infection The inventors established an assay for detecting viral infection. The inventors performed RNA in situ hybridization to detect both positive (+) and negative (−) strand virus RNA in the host cells after EV-A71 infection. As shown in FIG. 1A, both EV-A71 positive and negative RNA strands were detected after 7 h virus infection of HeLa cells. EV-A71 (−) RNA strand exhibited subtle co-localization with EV-A71 (+) RNA strand. On the other hand, double-stranded RNA, as shown by double-stranded RNA (DsRNA) immunostaining, exhibited strong co-localization with virus (−) RNA strand, not LAMP1, a lysosomal marker. Besides, DsRNA and (+) RNA were accumulated in time-dependent manner after virus infection (as shown in FIG. 1B). Thus, DsRNA immunostaining and viral specific (+) RNA hybridization can be applied to measure viral RNA replication.

Figure 1C:
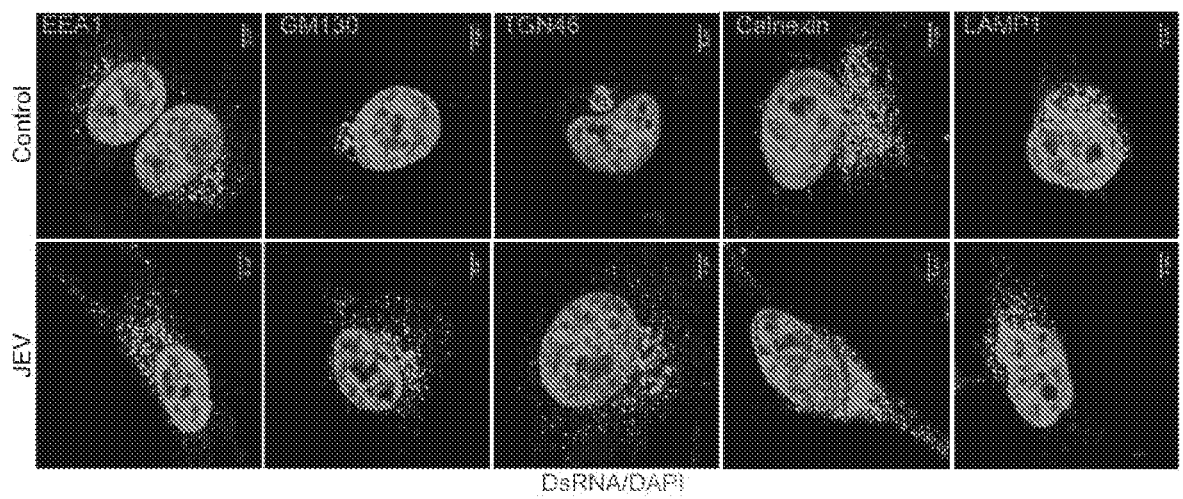
FIG. 1C shows the microscopic images of A549 cells, in which the A549 cells were infected with 10 MOI of JEV for 12 h, and stained with anti-double stranded RNA antibody and antibodies against different organelle markers, including early endosome marker EEA1, cis-golgi marker GM130, tran-golgi network marker TGN46, endoplasmic reticulum marker Calnexin, and lysosome marker LAMP1.

Besides EV-A71, the inventors also performed the aforementioned assays to measure ZIKV, JEV and DENV infection. The inventors particularly examined the localization of the virus replication in host cells by co-immunostaining the host cells after JEV infection with DsRNA antibody and antibodies against different organelle markers. As shown in FIG. 1C, DsRNA signal exhibited weak co-localization with early endosome (anti-EEIA staining), Golgi, endoplasmic reticulum (anti-Calnexin staining), or lysosome (anti-LAMP1 staining). These data suggested that JEV replication complex is located at a novel membrane structure in the host cell.

Accordingly, the inventors have established a valid immunostaining and a valid RNA hybridization assay to measure positive single strand RNA virus replication. This assay was applied to determine the antiviral effect of alkaloids against various viral infections, which is described in detail below.

Determination of the Role of $Ca^{2+}$ Signaling in Viral Infection

Figure 1D:
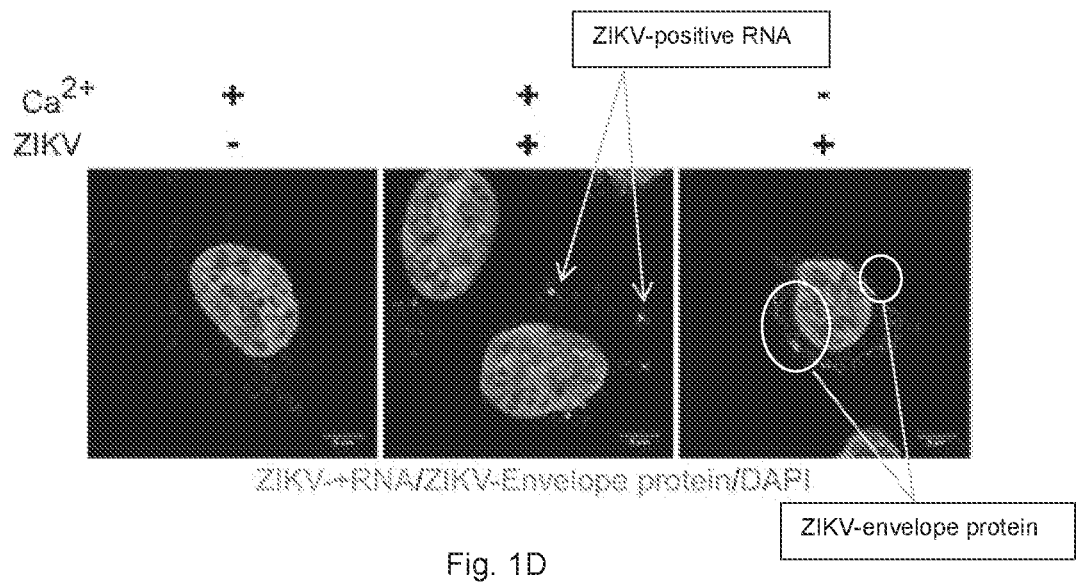
FIG. 1D shows the microscopic images of A549 cells infected with ZIKV in the presence or absence of extracellular calcium ions.

The inventors determined whether removal of extracellular $Ca^{2+}$ affects ZIKV infection of host cells by performing ZIKV H+RNA hybridization and anti-ZIKV envelope protein immunostaining. As shown in FIG. 1D, ZIKV+RNA was detectable inside host cells after 90 minutes of viral infection in the presence of extracellular $Ca^{2+}$, whereas no positive viral RNA was detected in host cells after 90 minutes of the viral infection in the absence of extracellular $Ca^{2+}$. Moreover, in the host cells in the absence of extracellular Ca2+, intact virirons (staining with ZIKV envelope proteins) were detected in the plasma membrane of host cells as shown in the right panel of FIG. 1D. These results suggest that Ca2+ influx is required for flavivirus entry of host cells.

Figure 1E:
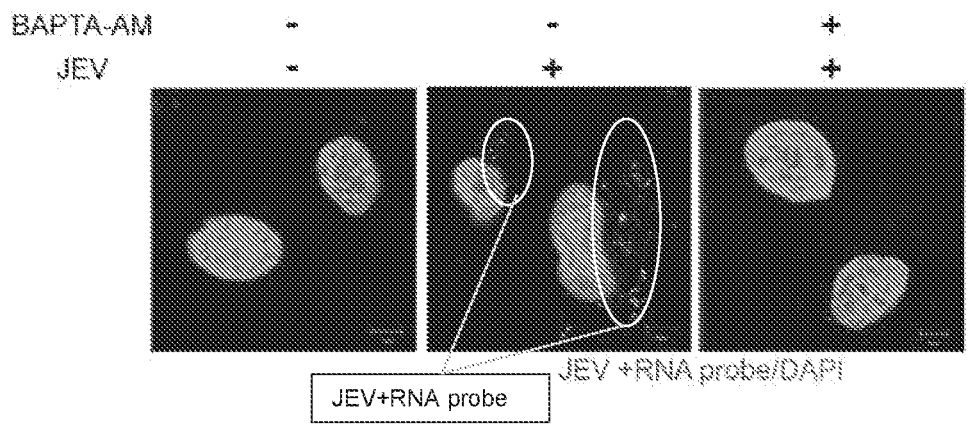
FIG. 1E shows the microscopic images of A549 cells infected with JEV after treatment with BAPTA-AM, a calcium chelator, in which the presence of absence of JEV positive RNA strand is detected.
Figure 1F:
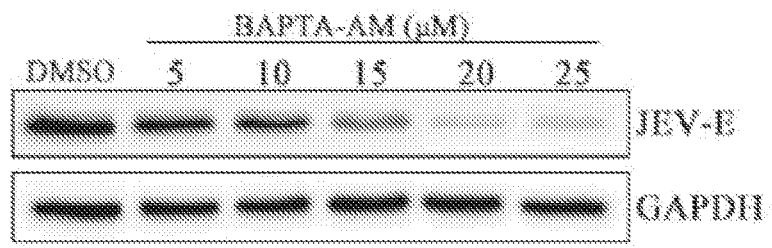
FIG. 1F is a Western blot pattern showing that BAPTA-AM treatment inhibited the JEV envelope protein synthesis in the A549 cells in a dose dependent manner.

With reference to FIG. 1E, in cells treated with BAPTA-AM, a calcium chelator, no ZIKV positive RNA strand was spotted inside the host cells. It was also found that BAPTA-AM treatment of host cells markedly inhibited the expression of JEV envelope protein in a dose dependent manner, as shown in FIG. 1F. Again, these date suggest that intracellular calcium signaling is involved in flavivirus infection of host cells. Similar data have also been observed for EV-A71 infection of host cells (data not shown). These data together support the role of $Ca^{2+}$ influx or intracellular $Ca^{2+}$ in flavivirus or enterovirus infections.

High-Content Image Based Assay for Measuring Viral Infection

Figure 2A:
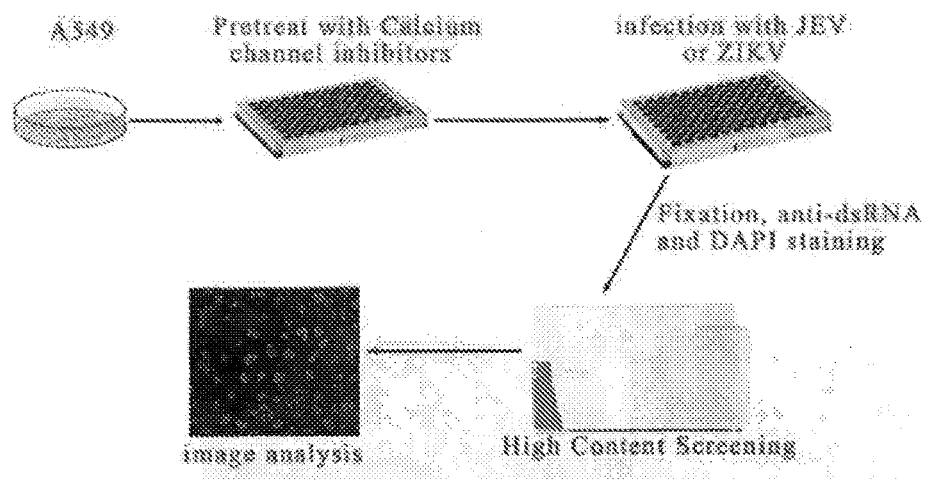
FIG. 2A illustrates the high-content image assay based on DsRNA immunostaining performed by the user for the purpose of measuring viral infection in host cells.

To measure flavivirus or enterovirus infection of host cells, the inventors developed a high-content image assay to measure DsRNA staining of virus infected cells by an automatic fluorescence microscopy, thereby quantifying flavivirus or enterovirus infection. The scheme of the measurement is illustrated in FIG. 2A. Particularly, the cells are pre-treated with a calcium channel inhibitor before being subject to viral infection. After viral infection, the cells are fixed. DsRNA immunostaining is then performed on the fixed cells, followed by high-content screening and image analysis.

This assay was then applied to screen compounds affecting viral infection, as follows. Host cells, e.g. A549, RD, PC3, or JEG-3 cells, were seeded in 96-well plates in triplicates, and cells were then pretreated with different compounds at different concentrations for 1 h before being infected with about 10 to about 100 MOI of JEV, ZIKV, or EV-A71 virus. After 8 to 24 h of infection, cells were fixed with 4% PFA and subject to DsRNA immunostaining and DAPI staining. The images were finally captured by CellInsight CX7 High-Content Screening platform with a 20× objective lens, and analyzed in HCS Studio™ 3.0 (Thermo Fisher, Waltham, MA, USA) to quantify the percentage of infected cells versus uninfected cells.

Figure 2B:
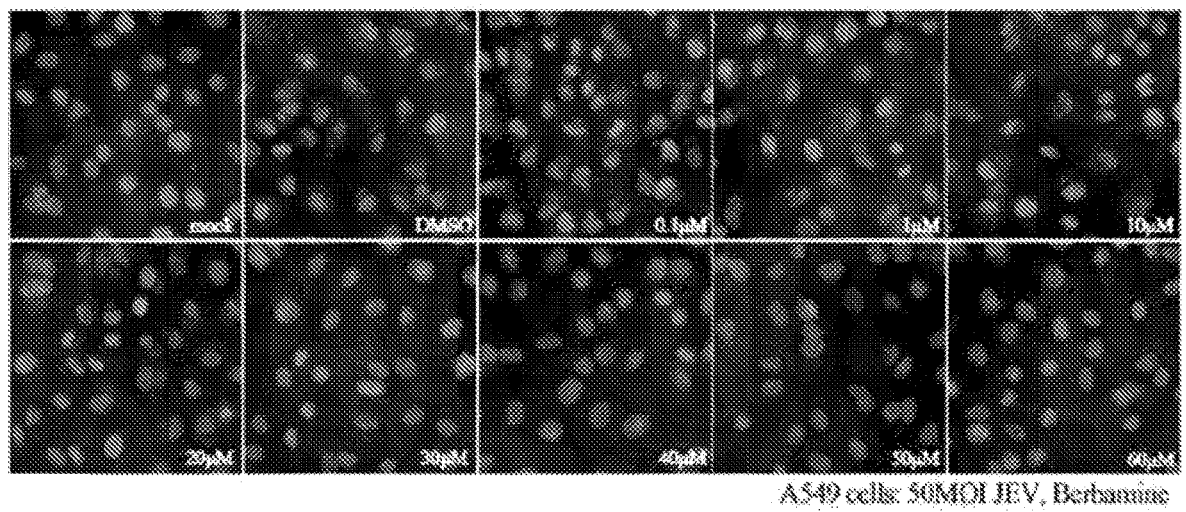
FIG. 2B shows the high-content images of A549 cells after pretreating A549 cells with indicated dose of berbamine for 1 h and infected with 50 MOI of JEV for 18 h, and a dose responsive curve of berbamine on JEV.
Figure 2B:
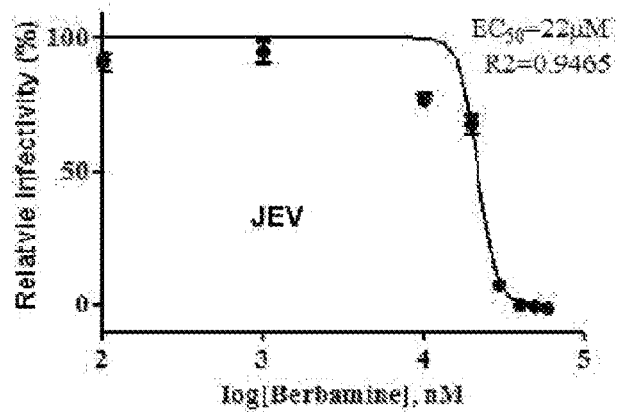

Inhibitory effect of berbamine and its analogues against ZIKV or JEV infection The inventors determined the anti-infection activity of berbamine, a bis-benzylisoquinoline alkaloid isolated from the traditional Chinese medicine berberis, against ZIKV or JEV infection. As shown in FIG. 2B, berbamine, the alkaloid of Formula (I), significantly inhibited the infection of JEV in A549 cells, with $EC_{50}$ being 20 μM.

Formula (I)

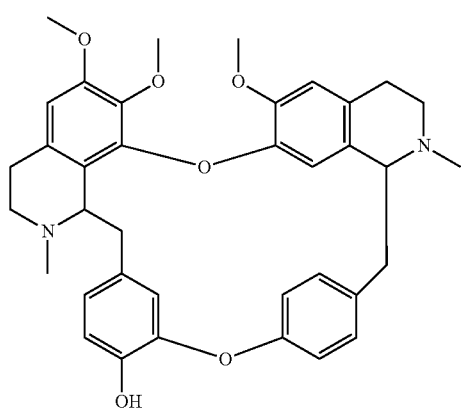

Figure 2C:
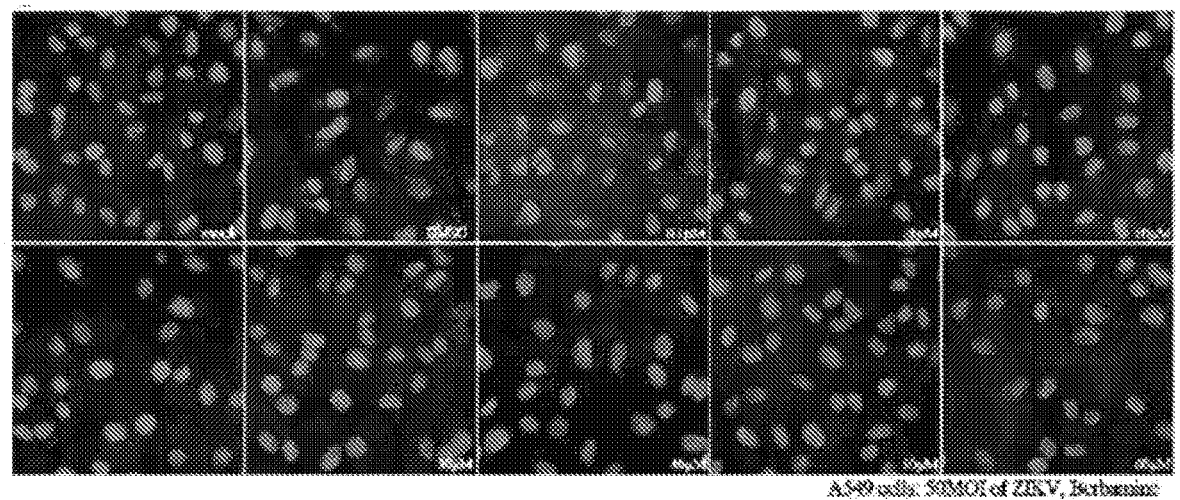
FIG. 2C shows the high-content images of A549 cells after pretreating A549 cells with indicated dose of berbamine for 1 h and infected with 50 MOI of ZIKV for 18 h, and a dose responsive curve of berbamine on ZIKV.
Figure 2C:
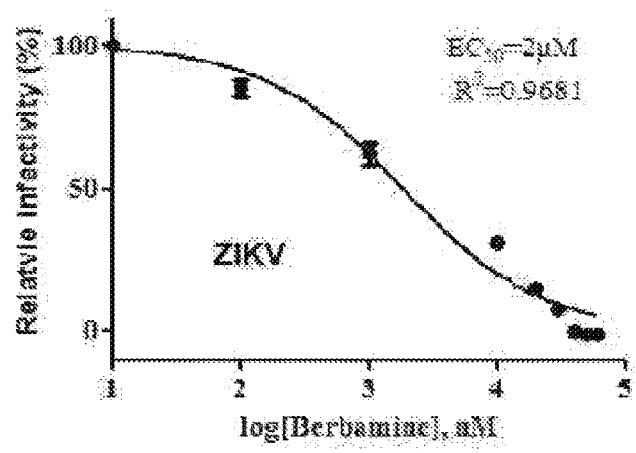
Figure 2D:
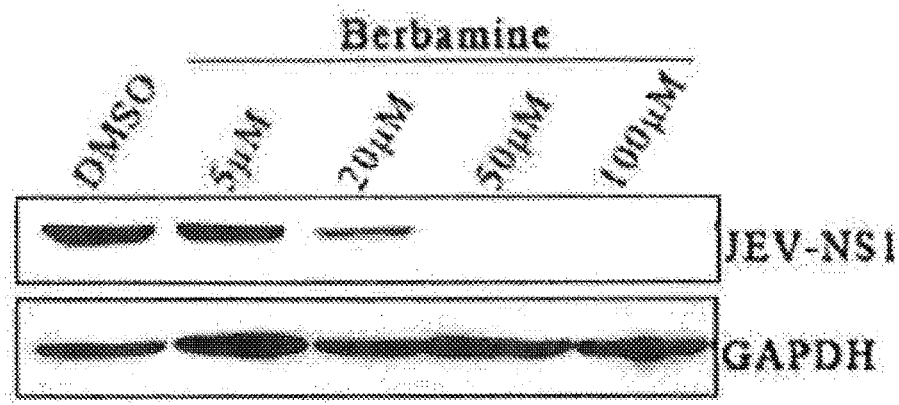
FIG. 2D is a Western blot pattern showing the expression of JEV-NS1 in A549 cells which were pretreated with berbamine at indicated dose for 1 h and infected with ~10 MOI JEV for 10 h, and the expression of JEV-NS1 in A549 cells which were pretreated with DMSO as control group.
Figure 2E:
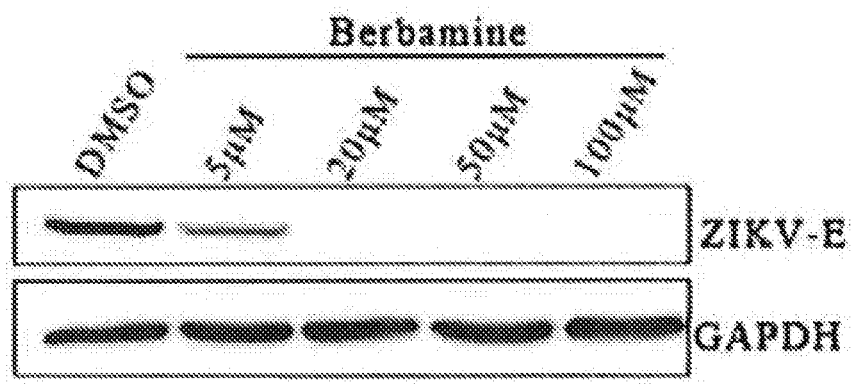
FIG. 2E is a Western blot pattern showing the expression of ZIKV-E in A549 cells which were pretreated with berbamine at indicated dose for 1 h and infected with ~10 MOI ZIKV for 10 h, and the expression of ZIKV-E in A549 cells which were pretreated with DMSO as control group.
Figure 2F:
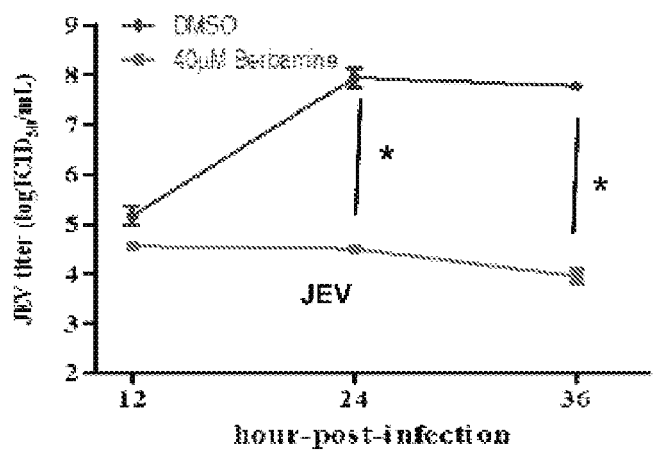
FIG. 2F is a plot of JEV titer against post-treatment time, after pretreating A549 cells with berbamine, in which berbamine markedly inhibited JEV virus production.
Figure 2G:
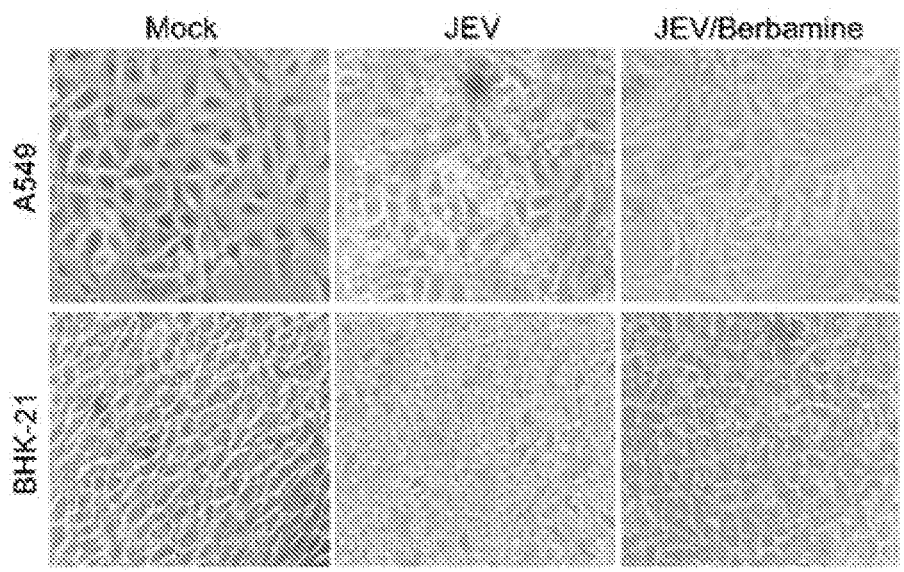
FIG. 2G includes microscopic images of A549 cells and BHK-21 cells after JEV infection with/without berbamine pretreatment.

FIG. 2C also demonstrates that berbamine inhibited the infection of ZIKV in A549 cells, with $EC_{50}$ being 2 μM. Moreover, as shown in FIGS. 2D and 2E, the pre-treatment of cells with berbamine markedly inhibited the protein expression of JEV-NS1 and ZIKV-E in a dose dependent manner. The inventors further performed a virus titration assay and confirmed that pretreatment of cells with berbamine significantly inhibited the production of JEV according to the results in FIG. 2F. FIG. 2G also shows that the pretreatment of A549 cells or BHK-21 cells with berbamine markedly reduced JEV-induced cell death. These data indicated that berbamine has inhibitory effect against both JEV and ZIKV infection in host cells.

Figure 3A:
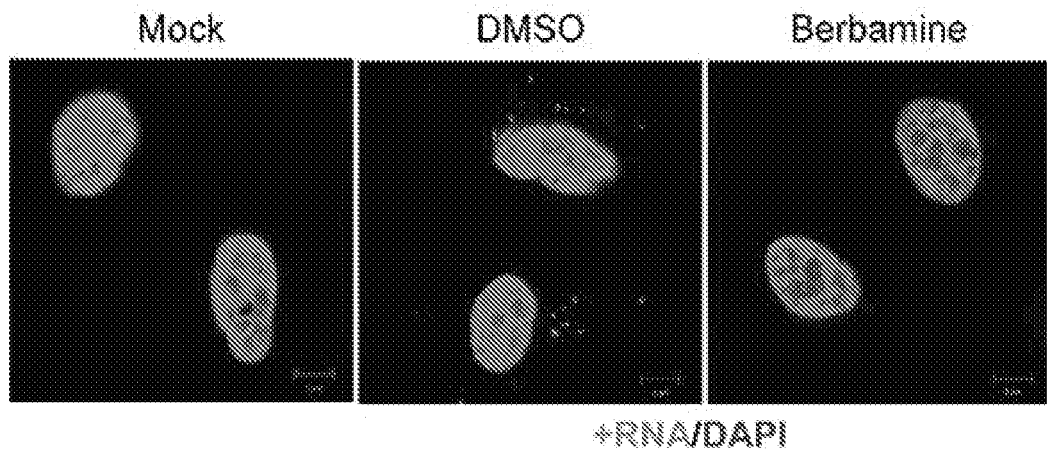
FIG. 3A shows the microscopic images of A549 cells after immunostaining, in which the cells were pretreated with berbamine for 1 h, then infected with 100 MOI of JEV for 80 min before fixation and staining. The encircled pattern refers to the presence of RNA genome of JEV.

Furthermore, as demonstrated in FIG. 1D, calcium influx is required for the entry of JEV or ZIKV. The inventors further determined whether treatment of host cells with berbamine can block the entry of these viruses. To evaluate this, A549 cells were pre-treated with berbamine for 1 h, and were then infected with JEV for 80 min before fixation. Viral positive strand RNA hybridization was subsequently performed to detect the RNA genome of JEV. The results in FIG. 3A show that the positive strand JEV RNA was only detected inside control cells, not in cells pretreated with berbamine.

Figure 3B:
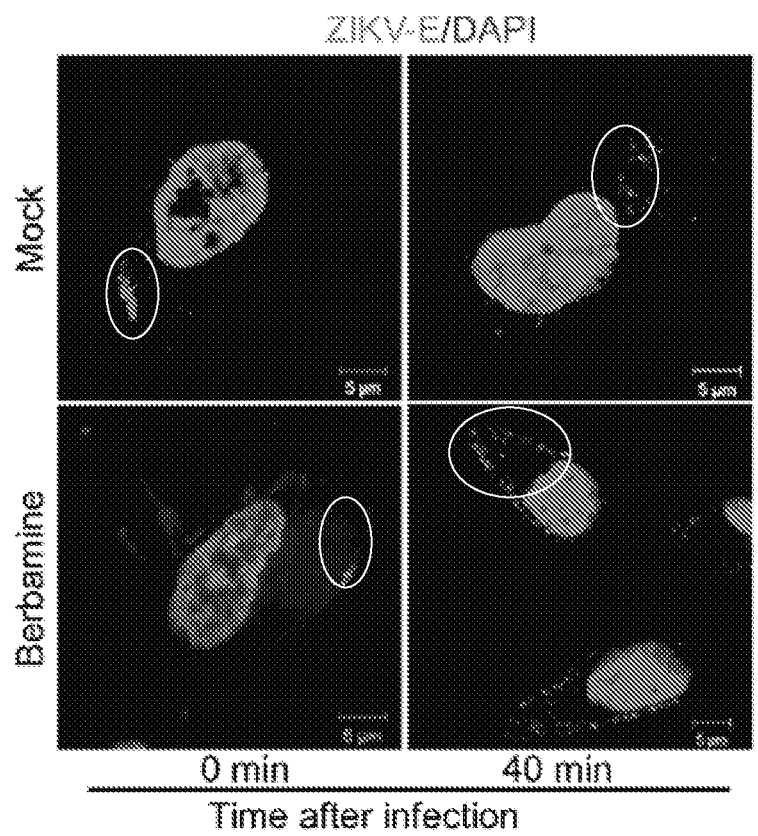
FIG. 3B shows the microscopic images of A549 cells after immunostaining, in which the cells were pretreated with berbamine, then infected with 100 MOI of ZIKV on ice for 1 h followed by incubation in warm medium for the indicated time course before fixation and staining. The arrows point to the presence of ZIKV.

Also, A549 cells pretreated with or without berbamine were incubated with ZIKV on ice for 1 h, and were then incubated with warm medium at 37° C. for another 40 min before fixation, followed by anti-ZIKV envelope protein immunostaining. The results in FIG. 3B show that the intact ZIKV virus (encircled in the figure) was detectable on the surface of virus infected cells pretreated with or without berbamine, whereas the intact ZIKV virus were highly concentrated at the surface of virus infected cells pretreated with berbamine, not the control cells, after cells were incubated at warm medium. Accordingly, these data demonstrate that berbamine have inhibitory effect against the entry of ZIKV or JEV into host cells.

The inventors further tested three analogues of berbamine including isotetrandrine, fangchinoline, and E6 berbamine to see if they have anti-infection effect against the flavivirus particularly JEV and ZIKV.

Isotetrandrine

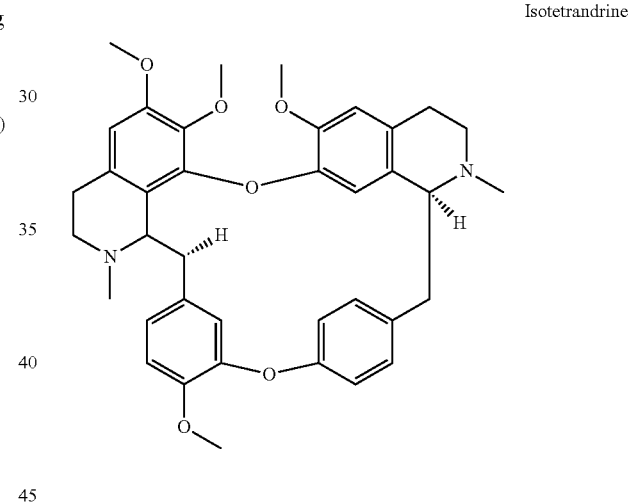

Fangchinoline

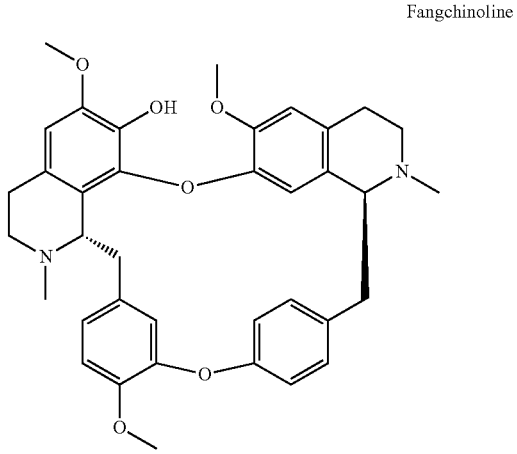

-continued

E6 berbamine

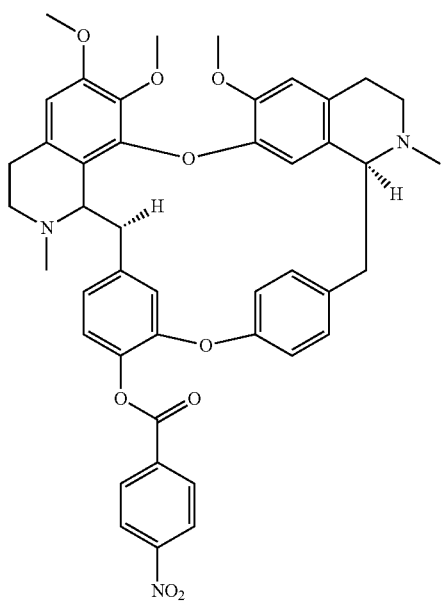

Figure 4A:
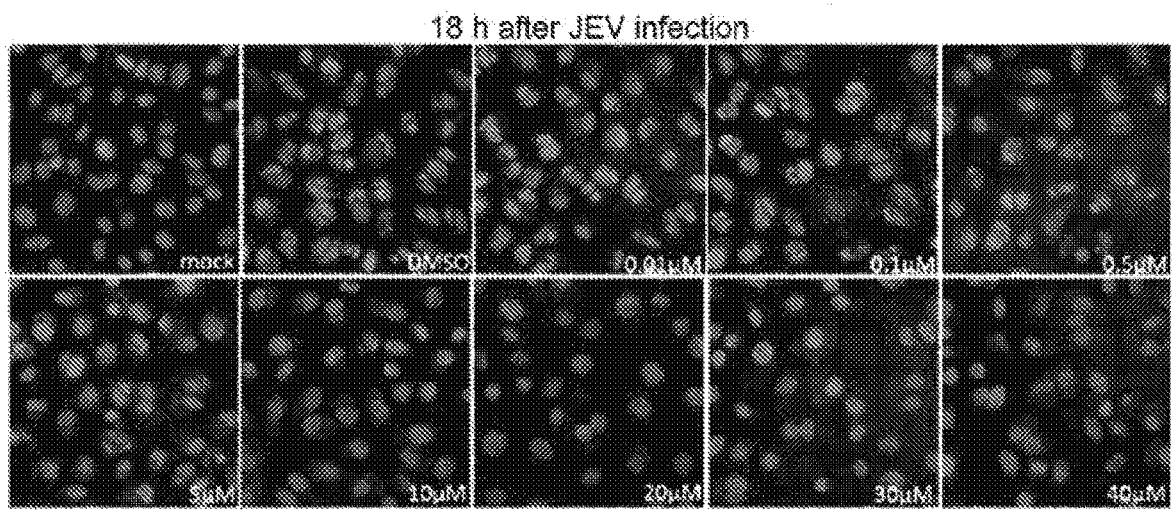
FIG. 4A shows the high-content images of A549 cells after immunostaining, in which the cells were pretreated with indicated doses of isotetrandrine for 1 h, then infected with about 50 MOI of JEV.
Figure 4B:
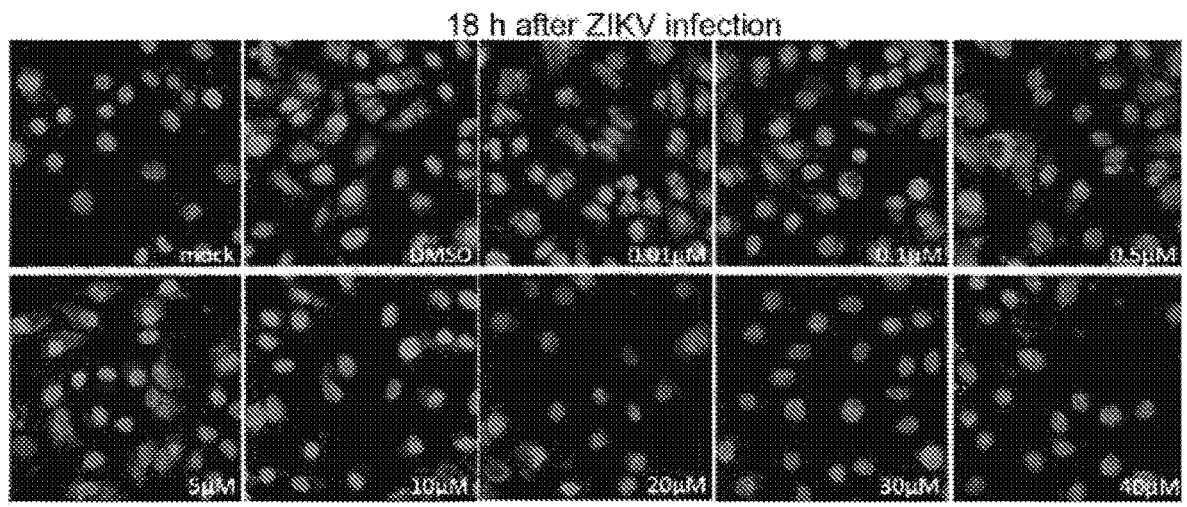
FIG. 4B shows the high-content images of A549 cells after immunostaining, in which the cells were pretreated with indicated doses of isotetrandrine for 1 h, then infected with about 50 MOI of ZIKV.
Figure 4C:
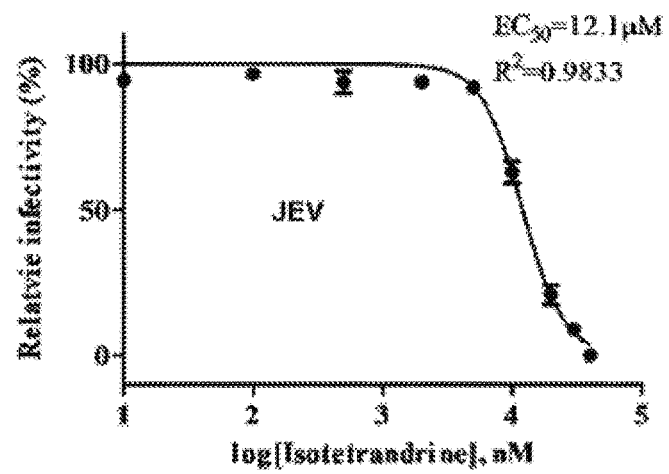
FIG. 4C is plot showing the relative infectivity of JEV in 549 cells in the treatment of isotetrandrine at different doses, wherein the $EC_{50}$ of isotetrandrine against JEV in A549 cells is around 12 μM.

As shown in FIGS. 4A to 4C, it was found that isotetrandrine significantly inhibited both JEV and ZIKV infections of host cells. Referring to FIG. 7C, the EC50 of isotetrandrine against JEV in A549 cells is around 12 μM.

Figure 5A:
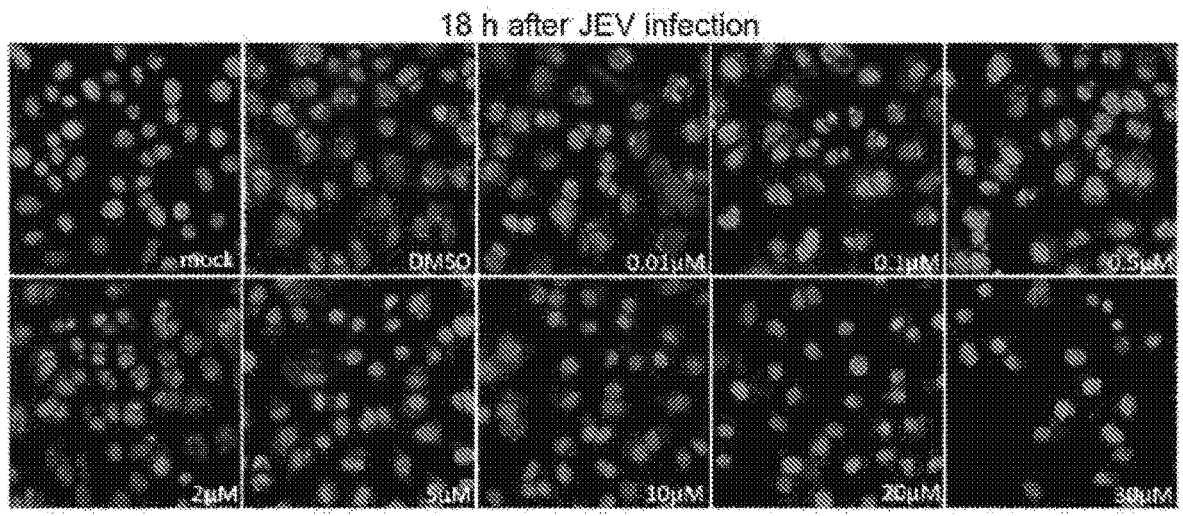
FIG. 5A shows the high-content images of A549 cells after immunostaining, in which the cells were pretreated with indicated doses of fangchinoline for 1 h, then infected with about 50 MOI of JEV.
Figure 5B:
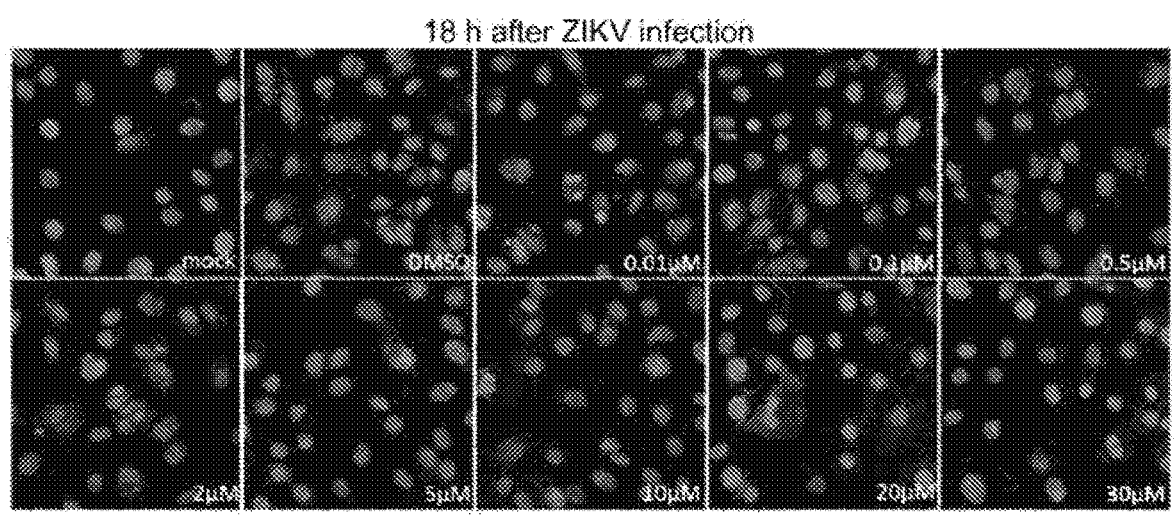
FIG. 5B shows the high-content images of A549 cells after immunostaining, in which the cells were pretreated with indicated doses of fangchinoline for 1 h, then infected with about 50 MOI of ZIKV.
Figure 5C:
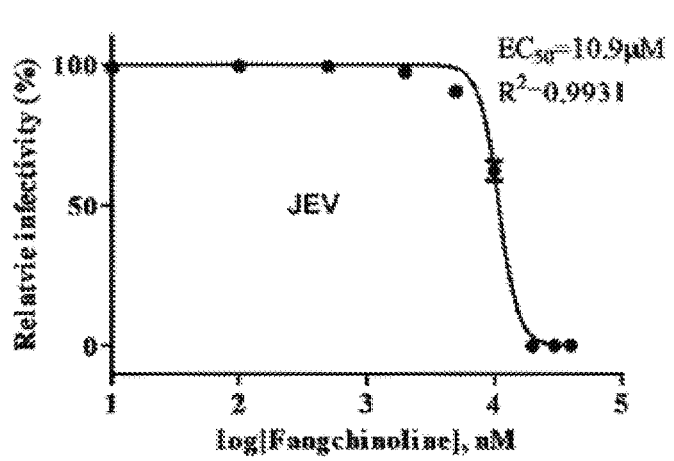
FIG. 5C is plot showing the relative infectivity of JEV in 549 cells in the treatment of fangchinoline at different doses, wherein the $EC_{50}$ of fangchinoline against JEV in A549 cells is around 11 μM.

As shown in FIGS. 5A to 5C, it was found that fangchinoline significantly inhibited both JEV and ZIKV infections of host cells. Referring to FIG. 8C, the EC50 of fangchinoline against JEV in A549 cells is around 11 μM.

Figure 6A:
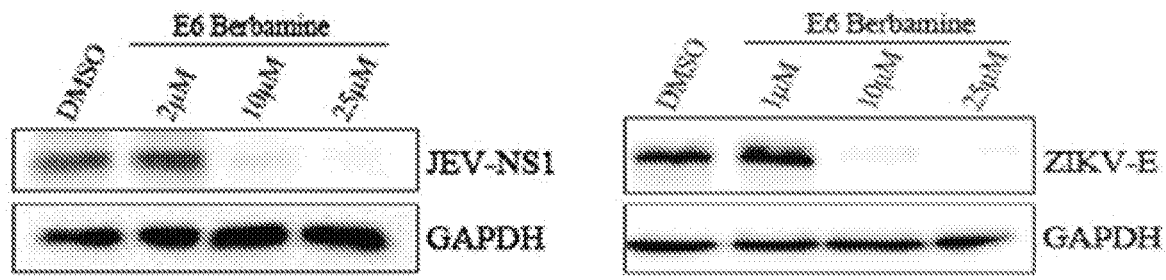
FIG. 6A is a Western blot pattern showing the expression of JEV-NS1 and ZIKV-E in A549 cells, in which the cells were pretreated with indicated doses of E6 berbamine for 1 h, then infected with about 50 MOI of JEV or ZIKV.

As shown in FIG. 6A, it was found that E6-berbamme markedly inhibited the infection of JEV or ZIKV, as manifested by strong inhibition of JEV-NSI and ZIKV-Envelope protein expression in host cells treated with E6-berbamine.

Figure 6B:
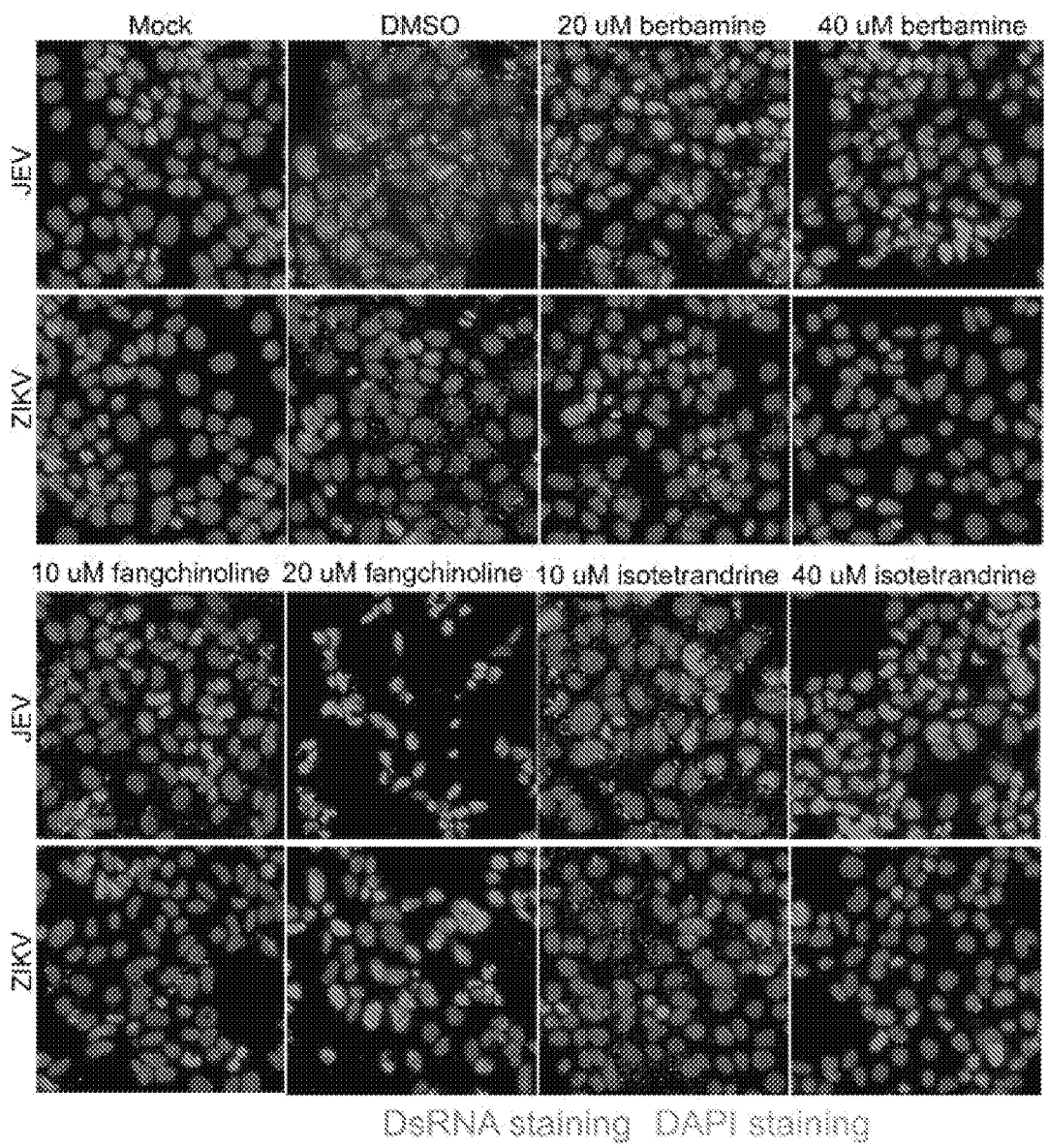
FIG. 6B shows the high-content images of JEG-3 cells after immunostaining, in which the cells were pretreated with 20 μM of berbamine, 40 μM of berbamine, 10 μM of fangchinoline, 20 μM of fangchinoline, 10 μM of isotetrandrine or 40 μM of isotetrandrine for 1 h, then infected with about 50 MOI of JEV or ZIKV for 18 h.

Moreover, the inventors determined their effect against JEV or ZIKV infection in another host cell line to ensure their anti-viral effects are not cell type specific. Referring to FIG. 6B, treatment of JEG-3 cells with berbamine, isotetrandrine, fangchinoline, and E6 berbamine all significantly inhibited JEV or ZIKV infection as shown by DsRNA immunostaining followed by high-content image analysis. Taken together, these data demonstrate that bis-benzylisoquinoline alkaloids are potent anti-JEV or anti-ZIKV agent in vitro.

Inhibitory Effect of Berbamine and Its Analogues Against DENV Infection

The inventors also studied whether berbamine and its analogues have any effects on DENV infection. Briefly, A549 cells plated in triplicates in 96-well plates were pretreated with different doses of berbamine (5 μM, 15 μM or 30 μM), fangchinoline (10 μM, 20 μM or 30 μM) or isotetrandrine (10 μM, 20 μM or 40 μM) for 1 h before infected with about 10 MOI of Dengue virus type 2 (DENV-2). Cells were then fixed at 24 h.p.i. and subjected to DsRNA immunostaining to detect DENV-2 replication.

Figure 7A:
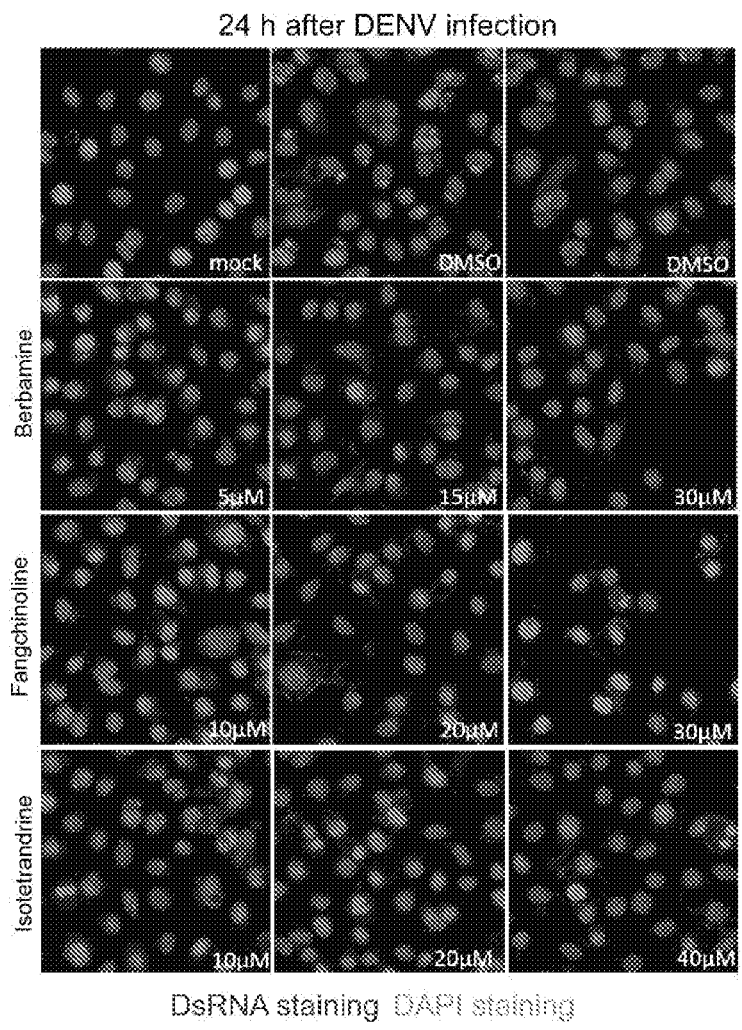
FIG. 7A shows the high-content images of A549 cells after immunostaining, in which the cells were pretreated with 5 μM of berbamine, 15 μM of berbamine, 30 μM of berbamine, 10 μM of fangchinoline, 20 μM of fangchinoline, 30 μM of fangchinoline, 10 μM of isotetrandrine, 20 μM of isotetrandrine or 40 μM of isotetrandrine for 1 h, then infected with about 10 MOI of DENV-2 for 18 h. High-content images of A549 cells of a control group pretreated with DMSO are also illustrated.
Figure 7B:
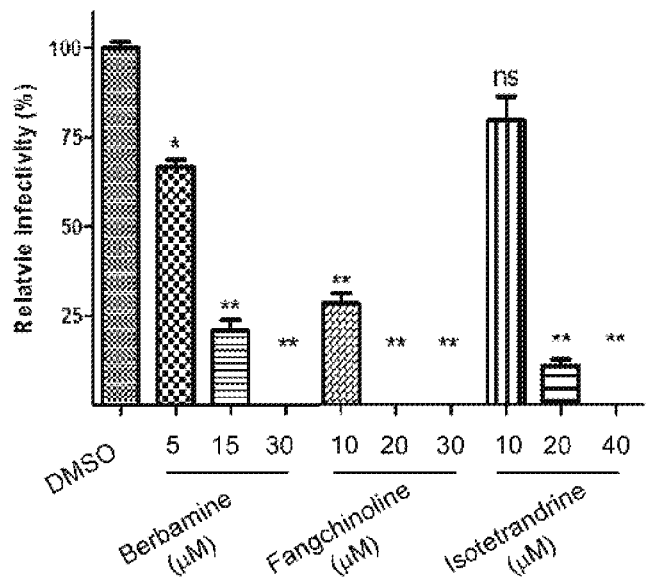
FIG. 7B is a plot showing the relative infectivity of DENV-2 in A549 cells, in which the cells were pretreated with indicated doses of berbamine, fangchinoline, or isotetrandrine for 1 h, then infected with about 10 MOI of DENV-2.

As shown in FIGS. 7A and 7B, all berbamine, isotetrandrine, and fangchinoline can significantly inhibit DENV-2 infection in A549 cells in a dose dependent manner. Taken together, these data demonstrate that berbamine and its analogues are potent anti-DENV agents and may be used as pan-anti-flavivirus agents.

Identification of Compounds with a Similar Structure by Virtual Screening

The inventors identified further 13 compounds via ligand-based virtual drug screening by using berbamine as reference. The identified 13 compounds are listed below.

TABLE 1

Identified additional compounds

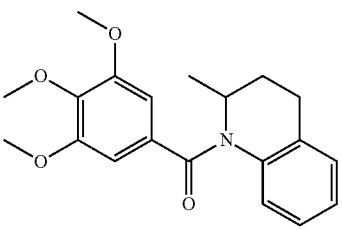 [SMILES: COc1cc(C(=O)N2c3ccccc3CCC2C)cc(OC)c1OC]
1

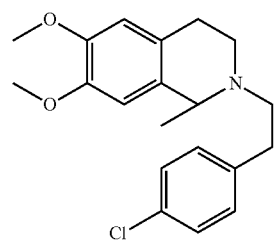 [SMILES: COc1cc2c(cc1OC)C(C)N(CCc1ccc(Cl)cc1)CC2]
2

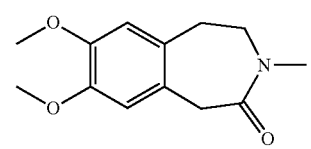
3

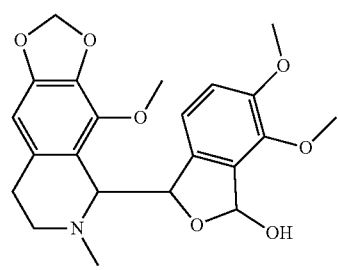 [SMILES: COc1ccc2c(c1OC)C(O)OC2C1c2c(cc3c(c2OC)OCO3)CCN1C]
4

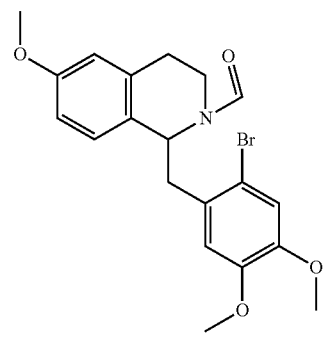 [SMILES: COc1ccc2c(c1)CCN(C=O)C2Cc1cc(OC)c(OC)cc1Br]
5

TABLE 1-continued

Identified additional compounds

6, #7, #8, #9, #10, #11, #12, #13

Figure 8A:
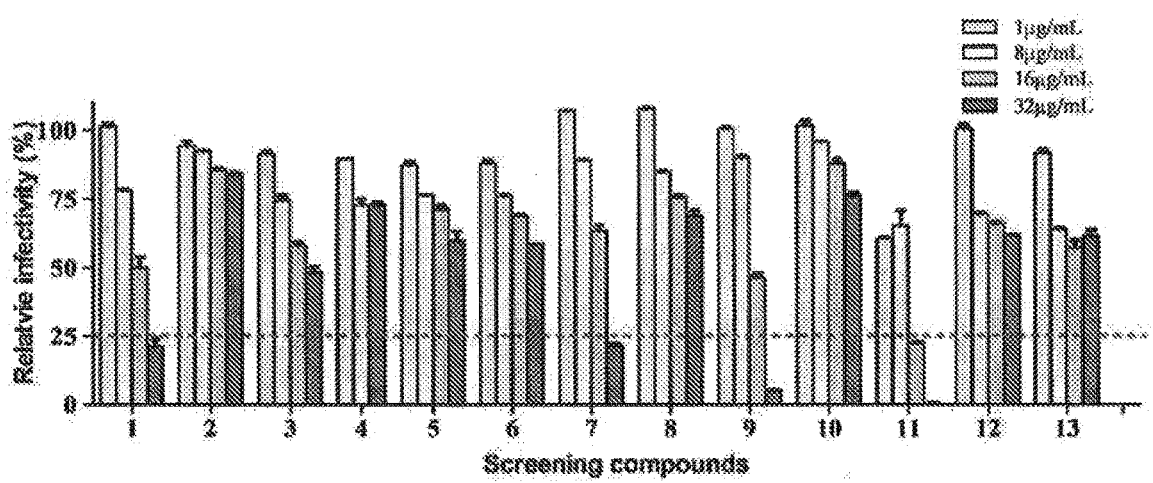
FIG. 8A is a plot showing the relative infectivity of JEV in A549 cells pretreated with 13 additionally identified compounds.
Figure 8B:
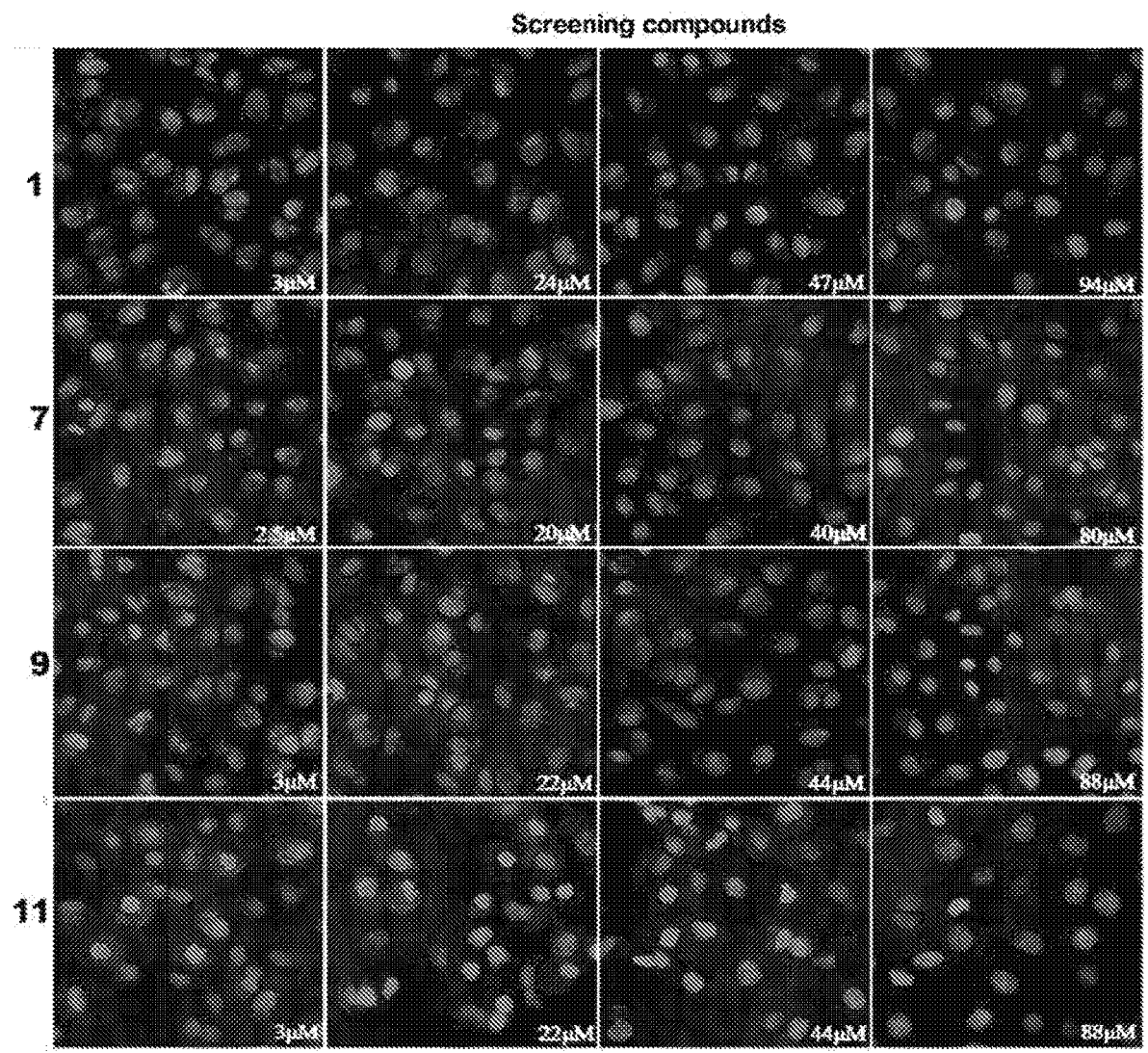
FIG. 8B shows the high-content images of A549 cells after immunostaining, in which the cells were pretreated with Compound #1, Compound #7, Compound #9 or Compound #11 respectively, then infected with about 50 MOI of JEV.

As shown in FIG. 8A, all these compounds have demonstrated an inhibitory effect against JEV infection in A549 host cells. Among them, 4 compounds including Compound #1, #7, #9 and #11 exhibited highest potency. As shown in FIG. 8B, these 4 compounds can effectively block the entry of JEV into the host cells.

Antiviral Effect Against JEV in Mice

Figure 9A:
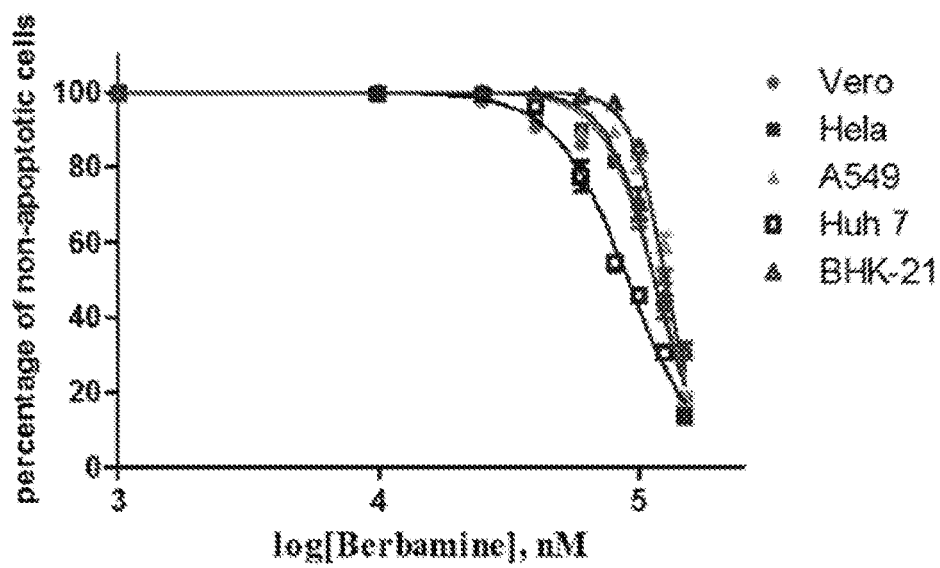
FIG. 9A shows the cytotoxicity of berbamine in A549 cells, BHK-21 cells, Vero cells, Hela cells, and Huh 7 cells.

The inventors determined the cytotoxicity of berbamine in different cell lines including A549 cells, BHK-21 cells, and RD cells. As shown in FIG. 9A and Table 2, it was found that berbamine has lowest cytotoxicity but highest therapeutic index as compared to other alkaloids (Table 3). The inventors therefore assessed the anti-JEV effects of berbamine in a mouse model.

TABLE 2

Cytotoxicity of berbamine in various cell lines.

| Cell Type | $CC_{50}$ (μM) |
| --- | --- |
| Vero | 114.936 ± 5.297 |
| Hela | 114.762 ± 3.596 |
| A549 | 126.629 ± 3.896 |
| Huh7 | 90.436 ± 2.977 |
| BHK-21 | 126.841 ± 2.426 |

TABLE 3

Selectivity index

| Virus | Selective Index ($CC_{50}/EC_{50}$) |
| --- | --- |
| ZIKV | 58.4 |
| JEV | 78.2 |
| SARS-CoV-2 | 48.9 |

Figure 9B:
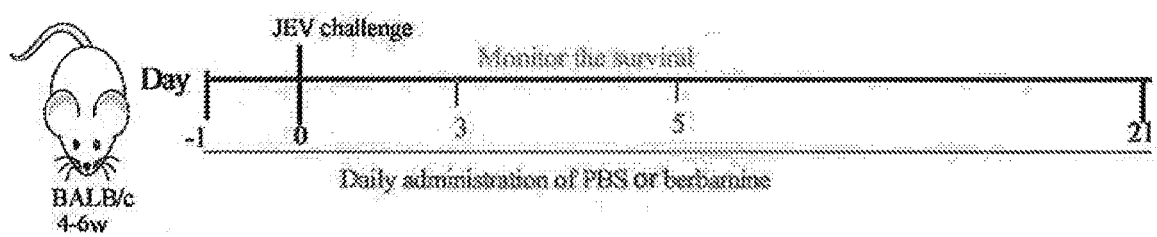
FIG. 9B illustrates the animal experiment, in which mice were injected with JEV, and then administered with PBS as the control group or berbamine as the treatment group.

As illustrated in FIG. 9B, adult female BALB/c mice (age, 4 to 6-week) mice were randomly divided into two groups (7 mice per group): a JEV-infected with vehicle-treated group and a
JEV-infected with berbamine-treated group. For infection, mice were injected intraperitoneally with approximately $10^{6.5}$ $TCID_{50}$ of JEV. For the berbamine treatment group, mice were injected intraperitoneally with a dose of 15 mg/kg berbamine or PBS daily. For the control-vehicle group, mice were injected intraperitoneally with a dose of 50 mg/kg PBS daily. Survival rate and change of body weight if the mice in each group were monitored for 15 days after JEV injection.

Figure 9C:
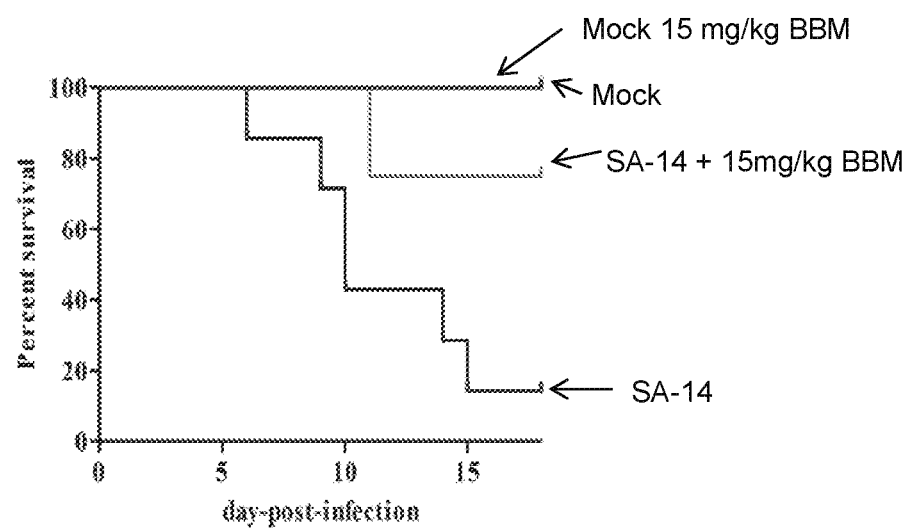
FIG. 9C shows the survival rate of mice after JEV challenge followed by treatment of berbamine for 15 days, in which the mock group and the mock group with 15 mg/kg of berbamine have the same survival rate.
Figure 9D:
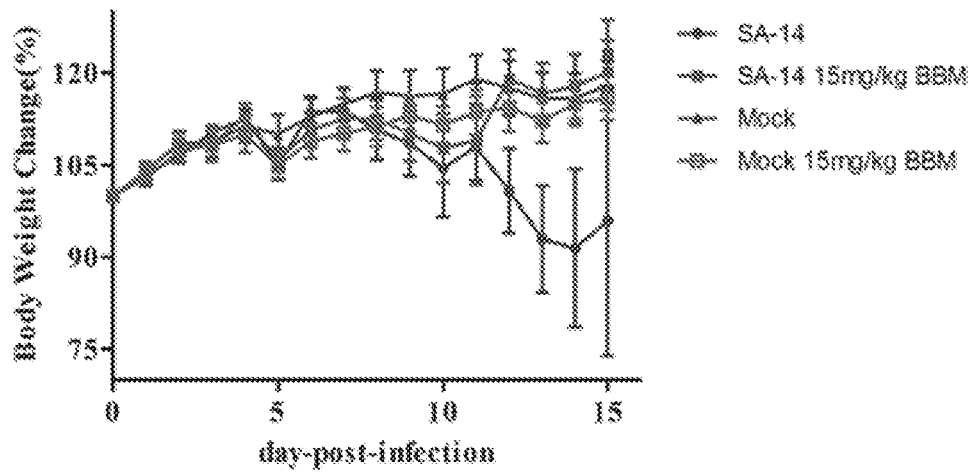
FIG. 9D shows the body weight change of mice after JEV challenge followed by treatment of berbamine for 15 days.

As shown in FIGS. 9C and 9D, berbamine treatment increases the survival rate of the mice, i.e. protect the mice from the lethal challenge of JEV. The higher survival rate and less weight changes in berbamine treatment group, as compared to the control group, further suggest that berbamine is a potential anti-flavivirus drug against JEV.

Inhibitory effect of berbamine and its analogues against enterovirus and lentivirus infections In addition, other than flavivirus infection, the inventors determined whether berbamine has any antiviral effect against enterovirus and lentivirus infection, by applying the same high-content image based assay as discussed above.

Figure 10:
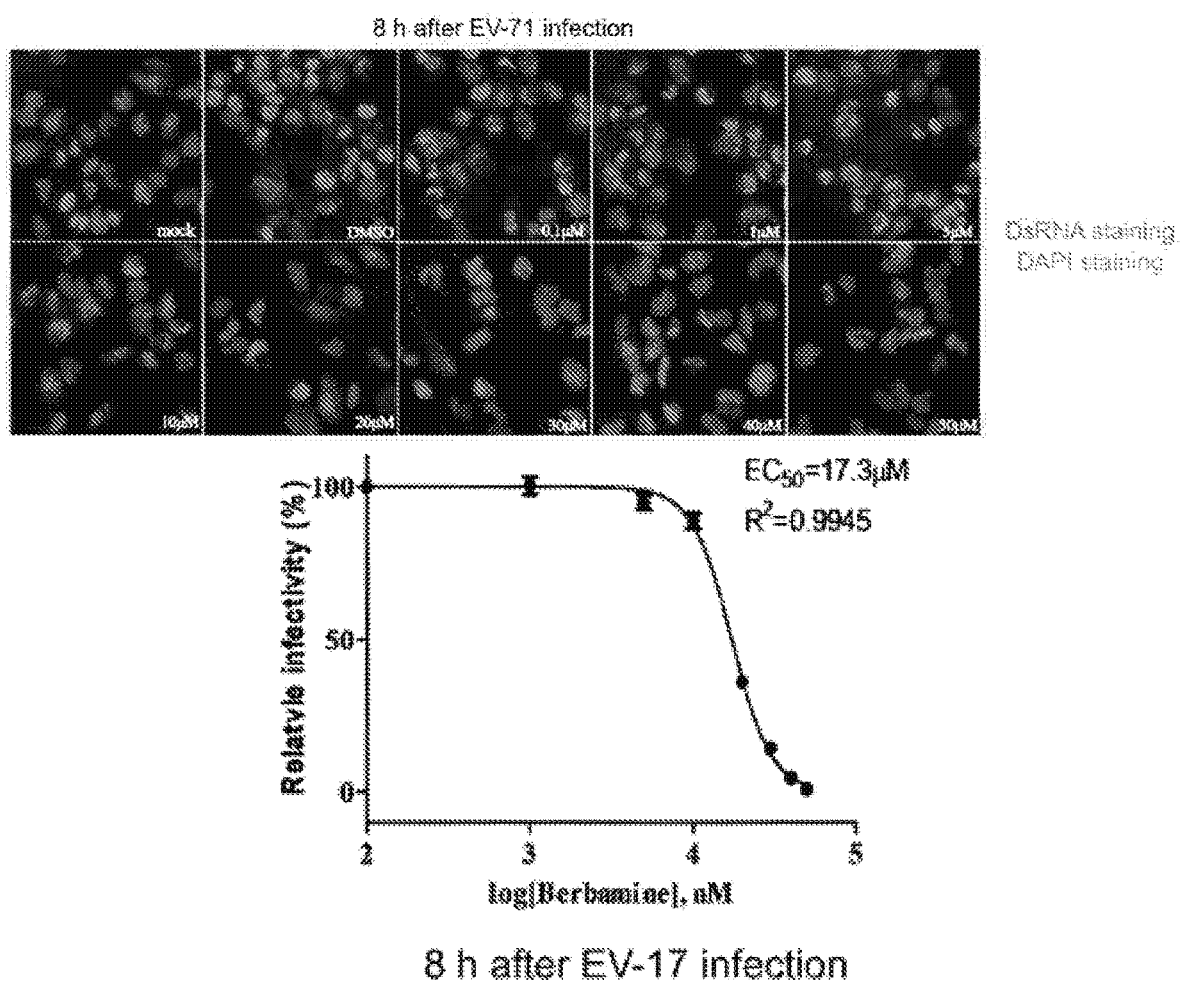
FIG. 10 shows the high-content images of RD cells after immunostaining, in which the cells were pretreated with berbamine with the indicated doses, and then infected with 10 MOI of EV-71, as well as a plot of relative infectivity of EV-71 in the pretreated cells with $EC_{50}$ being about 17.3 μM.

As shown in FIG. 10, berbamine treatment of RD cells significantly inhibited EV-A71 infection, with $EC_{50}$ being around 17 µM.

Figure 11:
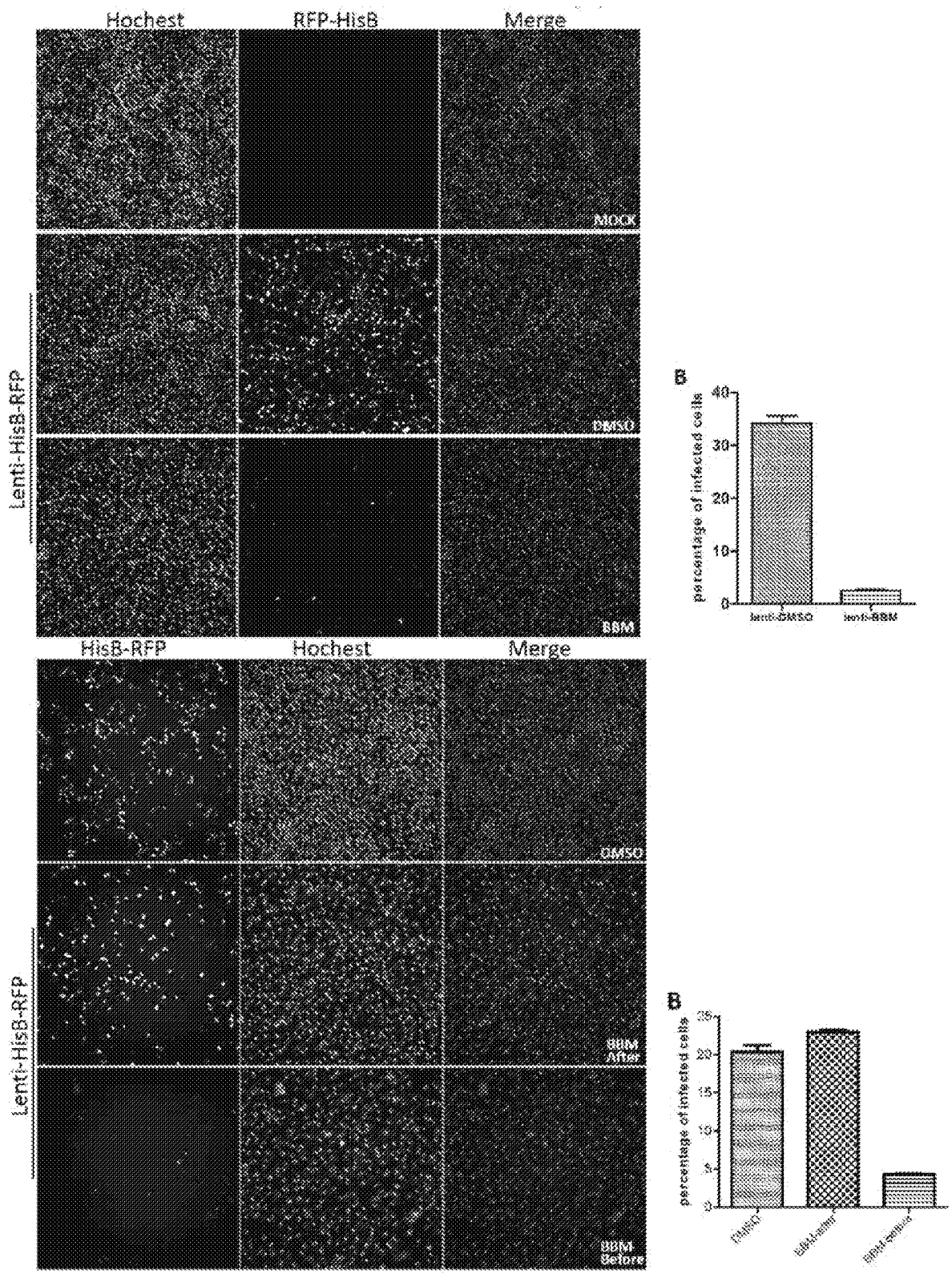
FIG. 11 shows the high-content images of A549 cells after immunostaining, in which the cells were pretreated with berbamine, and then infected with lentivirus encoding histone B-RFP; and the corresponding quantitative plot.

Further, pretreatment of A549 cells with berbamine also abolished lentivirus infection, as shown in FIG. 11.

Based on the above experimental results, it has been demonstrated that berbamine and its analogues particularly berbamine are potential anti-RNA virus agents.

II. Determination of Anti-Viral Effect of Berbamine Against Coronavirus

Coronavirus is an enveloped positive-sense single-stranded ((+)ss) RNA virus, and has four subgenus α, β, γ, and δ. The α and β coronavirus mainly infect mammals, while γ and δ coronavirus mainly infect birds, and a few of them can also infect mammals. The α and β coronavirus can cause respiratory or intestinal infections. Coronavirus has a very large (30 Kb)

RNA genome but only around 10 Kb is the coding region. This coding region encodes 4 structural proteins: spike (S) protein, membrane (M) protein, envelope (E) protein, nucleocapsid (N) proteins, as well as many non-structural proteins such as RNA-dependent RNA polymerase (RdRp) and helicase (Hel). Among them, the S protein is a trimeric glycoprotein, which can bind to the viral receptor of the host cells and is a key protein for the virus to enter the cells. Different coronaviruses may target different receptors.

SARS-CoV's S protein binds with angiotensin converting enzyme 2 (ACE2) to infect ciliated bronchial epithelial cells and type II lung epithelial cells. MERS-CoV's S protein interacts with dipeptidyl peptidase 4 (DPP4) to infect non-ciliated bronchial epithelial cells, bronchiolar epithelial cells, alveolar epithelial cells, and endothelial cells. Recently, it has been reported that SARS-CoV-2 infects human respiratory epithelial cells via its S-protein binding to human ACE2 followed by the receptor-mediated internalization. A transmembrane serine protease TMPRSS2 and other proteases, e.g. furin, are likely involved in SARS-CoV-2 entry of cells as well.

The inventors evaluated whether berbamine has any effect on endosomal trafficking system, so as to evaluate its inhibitory effect against the coronavirus. The endosomal trafficking system is comprised of a series of dynamically interconverted membrane-enclosed vesicular structures, including early endosome (EE), endosomal carrier vesicle (ECV)/multivesicular body (MVB), and late endosome (LE). When EEs mature to MVBs, the inward invagination of the membrane of MVBs forms the intraluminal vesicles (ILVs) inside the lumen of MVBs. During this process, some membrane proteins, e.g. CD81, CD63, and CD9, are incorporated into the invaginated membrane, while some cytosolic contents, e.g. proteins (TSG101, ALIX, HSP70, and HSP90), nucleic acid (RNA and DNA), metabolites, and amino acids, are enclosed inside ILVs. MVBs can either be delivered to lysosomes for degradation, or can fuse with plasma membrane to release its luminal ILVs. These released ILVs are called exosomes, a subset of extracellular vesicles (EVs) with sizes ranging from 40-150 nm. Another subset of EVs are the vesicles directly budding from cell plasma membrane with size ranging from 50-1000 nm. The cell-cell communications via the release and uptake of exosomes have been implicated in a number of physiological and pathological processes.

The TRPML family comprises three members: TRPML1, TRPML2 and TRPML3, and they share around ~40% amino acid sequence homology. They are non-selective cation channels, and are permeable to variety of cations, including $Ca^{2+}$, $Na^+$, $Zn^{2+}$ and $Fe^{2+}$. Loss-of-function mutations in TRPML1 lead to mucolipidosis type IV (ML4), a lysosomal storage disease. TRPMLs are located in the membrane of early endosomes and recycling endosomes, and they are especially rich in late endosomes and lysosomes. The activation of TRPMLs via PI(3,5)P2 can trigger the release $Ca^{2+}$ from endosomes and lysosomes, which participates in various endolysosomal trafficking events, including trafficking of endosomal vesicles, fusion events between late endosomes and lysosomes, and lysosome-mediated exocytosis.

The inventors via the following experiments found that berbamine potently supressed the infection of SARS-CoV-2 and MERS-CoV by inhibiting TRPMLs to decrease the levels of ACE2 and DPP4 at cell surface and thus preventing the entry of these viruses into the host cells. Accordingly, berbamine is a potential drug for preventing or treating a coronavirus infection. For instance, it may boost the immune system of a subject, and/or help delaying the on-set of a condition associated with the coronavirus infection in the subject.

Effect of Berbamine on Endolysosomal Trafficking

The S protein of SARS-CoV-2 or MERS-CoV binds with ACE2 or DPP4, respectively, to facilitate the viral particles entry into cells via receptor-mediated endocytosis. The inventors generated the murine leukemia virus (MLV)-based pseudotyped particles to incorporate S protein from either MERS-CoV or SARS-CoV-2 and express reporter genes, e.g. luciferase and/or RFP. MLV-SARS-CoV-2 S or MERS-SARS-CoV S pseudotyped particles effectively entered Huh7 or hACE2-overexpressed HEK293T cells, respectively, manifested by the expression of RFP and luciferase in cells.

Figures 12A, 12B, 12C:
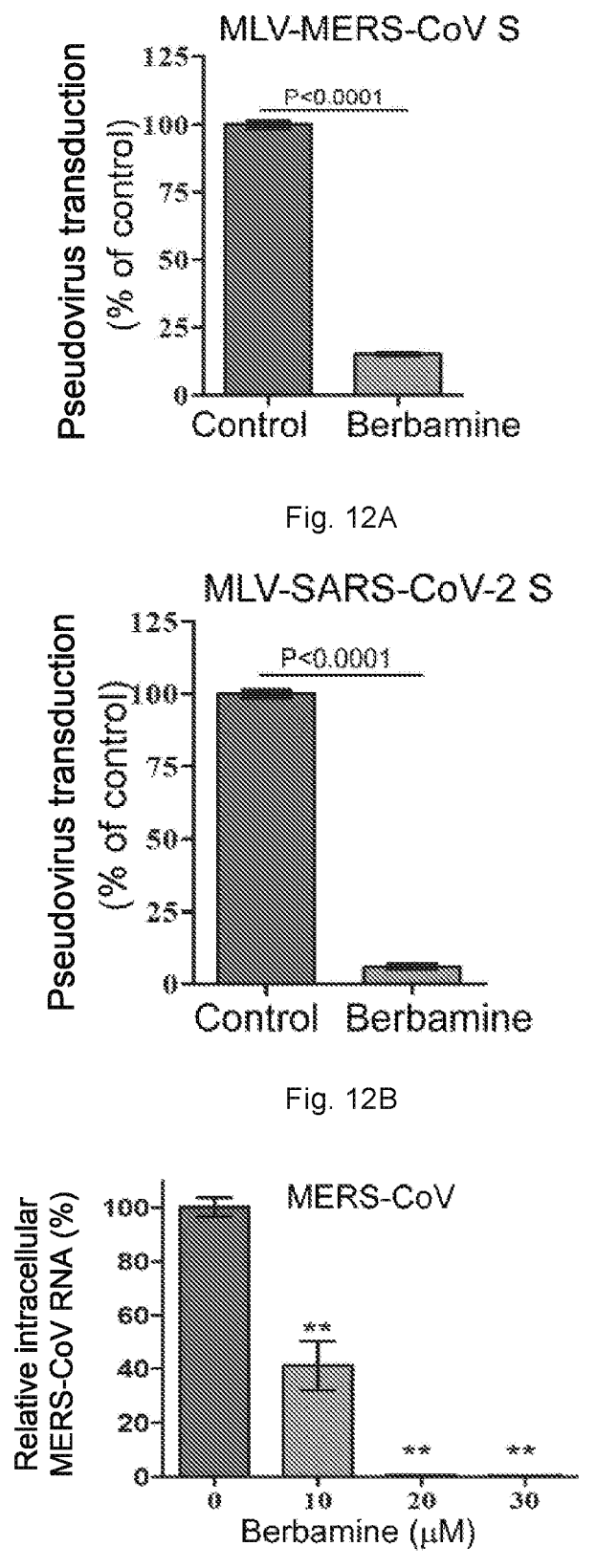

The inventors assessed the ability of berbamine to affect the entry of MLV-SARS-CoV-2 S or MERS-SARS-CoV S pseudotyped particles into host cells, and found that berbamine indeed effectively inhibited the entry of these psudoviruses (FIG. 12A and 12B).

Figure 12D:
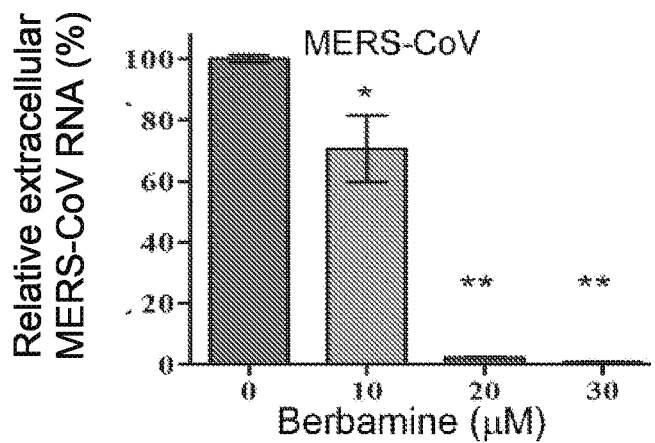
FIG. 12A shows that 10 μM berbamine inhibited the entry of pseudovirus particles MLV-SARS-CoV-2 S into Huh7 overexpressed HEK293T cells.
FIG. 12B shows that 10 μM berbamine inhibited the entry of pseudovirus particles MERS-SARS-CoV S into hACE2-overexpressed HEK293T cells.
FIG. 12C shows the relative intracellular MERS-CoV RNA level in supernatant of the sample after treating primary human lung fibroblast cells with berbamine at the indicated concentration, i
Figure 12E:
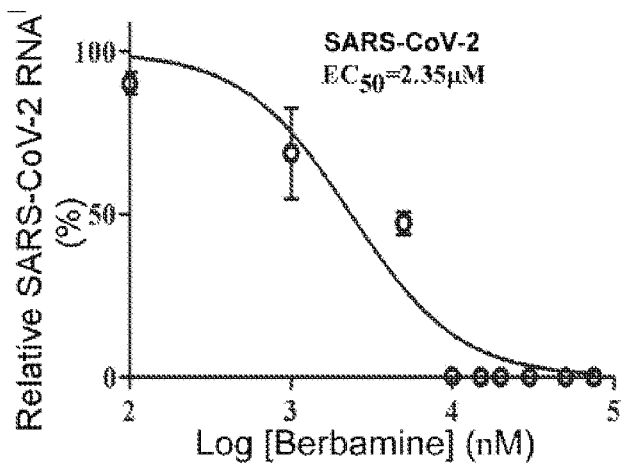
Figure 12F:
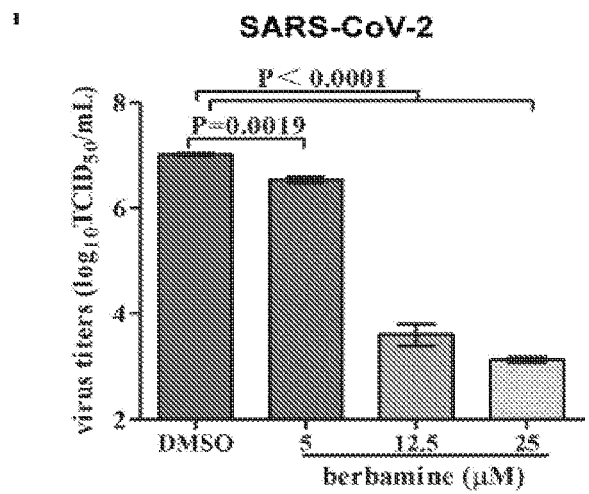

The inventors subsequently assessed the activity of berbamine against MERS-CoV and SARS-CoV-2 infection in vitro. Primary human lung fibroblasts were treated with berbamine and then infected with MERS-CoV, followed by qRT-PCR to measure the amount of intra- or extracellular viral RNA. The results show that berbamine significantly decreased both the intracellular (FIG. 12C) and extracellular (FIG. 12D) level of MERs-CoV RNA. The inventors also assessed the anti-SARS-CoV-2 activity of berbamine in Vero-E6 cells, and found that berbamine significantly inhibited the viral yield, as quantified by qRT-PCR assay (EC50=~2.3 µM) (FIG. 12E) or a virus titration assay (EC50=~4.7 μM) (FIG. 12F). In summary, these data indicate that berbamine is a potential drug against SARS-CoV-2 and MERS-CoV.

Interestingly, berbamine significantly inhibited the ability of Gly-Phe 3-naphthylamide (GPN) to trigger $Ca^{2+}$ release from lysosomes (FIG. 13A), which suggests that it inhibits lysosomal $Ca^{2+}$ channels. Since TRPMLs are one of main $Ca^{2+}$-permeable channels in lysosomes, the inventors assessed whether berbamine modulates TRPMLs-mediated $Ca^{2+}$ release from lysosomes. Treatment of cells with ML-SA1, a selective and potent TRPMLs agonist, markedly increased cytosolic $Ca^{2+}$ levels, and this ML-SA1-induced $Ca^{2+}$ increase was significantly inhibited by berbamine treatment (FIG. 13B). These results indicated that berbamine is a potential TRPMLs inhibitor.

Figure 15A:
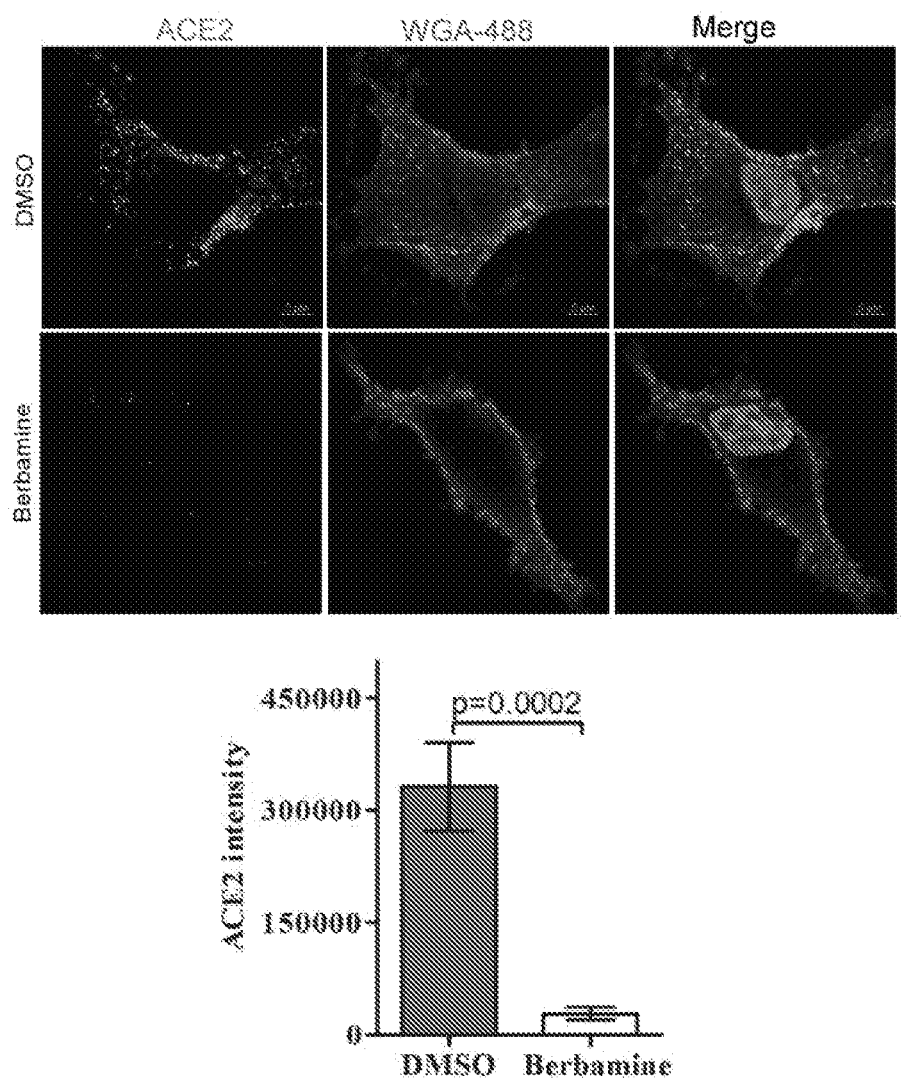
FIG. 15B shows the microscopic images of A549 cells treated with or without berbamine (50 µM) for the indicated times, followed by immunostaining of DPP4 and a plot indicating the relative ACE2 intensity.
FIG. 15C shows the expression of ACE2, DPP4, and HSP70 in Vero-E6 cells in the presence of cycloheximide (7.5 mg/ml) and being treated with/without berbamine (50 µM) for 6 h. The levels of ACE2, DPP4, and HSP70 in the cell lysates were determined by immunoblot analysis.
FIG. 15D shows the expression of ACE2, DPP4, and HSP70 in A549 cells in the presence of cycloheximide (7.5 mg/ml) and being treated with/without berbamine (50 µM) for 6 h. The levels of ACE2, DPP4, and HSP70 in the cell lysates were determined by immunoblot analysis.
FIG. 15E shows the expression of ACE2, DPP4, and ALIX in EVs collected from the culture medium of control or berbamine-treated A549 cells. The levels of ACE2, DPP4, and ALIX were determined by immunoblot analysis.
Figure 15B:
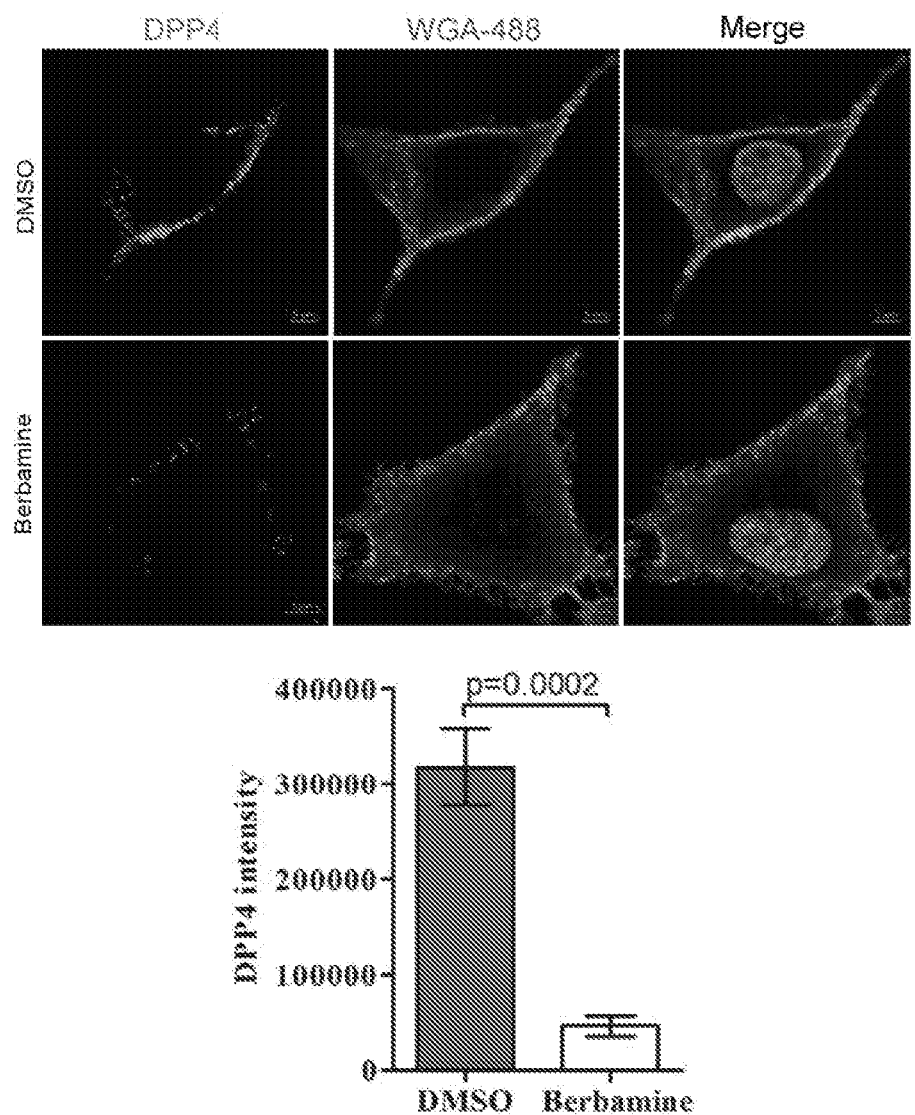

Since TRPMLs have been shown to participate in various endolysosomal trafficking events, it is possible that berbamine might inhibit TRPMLs to compromise the trafficking of ACE2, thereby preventing the entry of virus. The inventors, thus, examined whether berbamine changes the trafficking of ACE2. Briefly, cells were first incubated with an ACE2 antibody on ice for 90 min, and the internalization of the ACE2-antibody complex was then initiated at 37° C. for 2 h. In control cells, within 60 min, the ACE2-antibody complex had re-localized from the cell membrane to the late endosomes or lysosomes for degradation, as manifested by the co-localization of ACE2 and LAMP1, a late endosome/lysosome marker. After ~2 h, majority of the internalized ACE2-antibody complex was degraded in control cells (left panel in FIG. 13C). In contrast, following berbamine treatment, the ACE2-antibody complex failed to be sent to lysosomes for degradation (right panels in FIG. 13C). Thus, these data indicate that berbamine inhibits the endolysosmal degradation of ACE2. It is believed that the inhibition of ACE2 endolysosmal degradation by berbamine might affect its levels at the cell surface. By immunolabeling ACE2 in cells treated with or without berbamine followed by flow cytometric analysis or confocal imaging, the results show that berbamine indeed significantly decreased the levels of ACE2 at the plasma membrane (FIGS. 13D and 15A). Similarly, berbamine treatment significantly decreased the levels of DPP4 at plasma membrane (FIGS. 13E and 15B).

These results suggest that berbamine prevents SARS-CoV-2 or MERS-CoV from entering host cells by decreasing the levels of ACE2 or DPP4 at the plasma membrane.

Figure 15C:
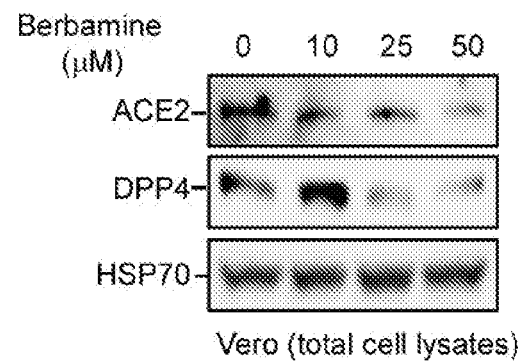
Figure 15D:
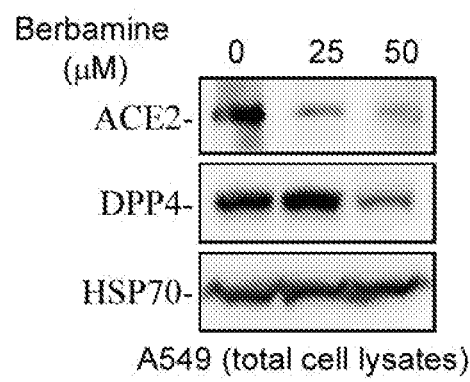
Figure 15E:
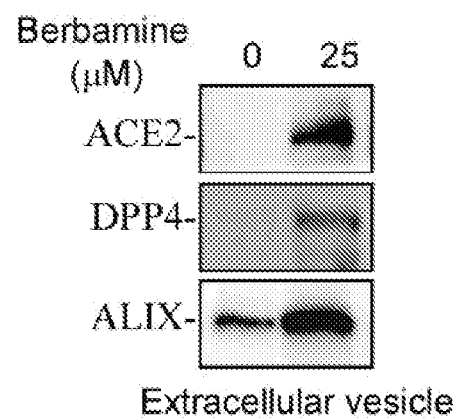

Interfering endolysomal trafficking has been shown to promote the exosome release, the inventors, thus, quantified the concentration of EVs in the cell culture medium of control or berbamine-treated cells using a nanoparticle analyzer. As expected, berbamine significantly promoted the secretion of EVs in Huh7 cells (FIG. 13F). The inventors then examined whether these EVs contain elevated levels of ACE2 or DPP4 in the berbamine-treated group when compared with the control group. Thus, EVs in the culture medium from the control and berbamine-treated Huh7 cells were collected by ultracentrifugation, and the protein levels of ACE2 and DPP4 were analyzed by immunoblot analysis. The results show that the levels of ACE2 and DPP4, similar to other exosome protein markers, e.g. TSG101, CD63, and Alix, were markedly increased in EVs collected from the berbamine-treated cell culture medium, when compared with the control group (FIG. 13G). The inventors also speculated that the increase in the secretion of ACE2 and DPP4-containing exosomes out of cells might lead to the reduced levels of these receptors in berbamine-treated cells. Indeed, when compared with the control cells, berbamine treatment markedly decreased the levels of ACE2 and DPP4 in Vero-E6 cells (FIG. 15C). Similar results regarding the effects of berbamine on the expression of ACE2 in cells or EVs have also observed in A549 cells (FIGS. 15D and 15E). Taken together, these results suggest that berbamine inhibits the endolysosomal trafficking of ACE2 or DPP4. This leads to an increase in the level of secretion of ACE2 or DPP4 via EVs and a concomitant decrease in their levels at the plasma membrane.

Figure 14A:
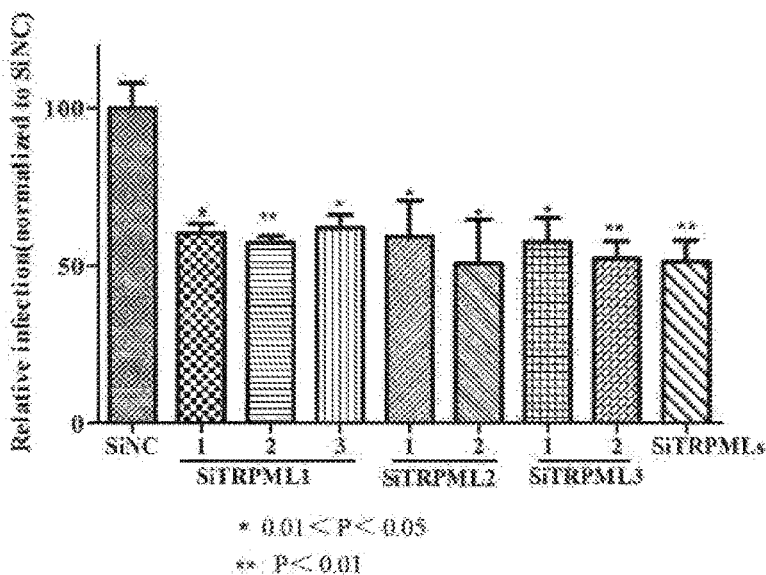
Figure 14A:
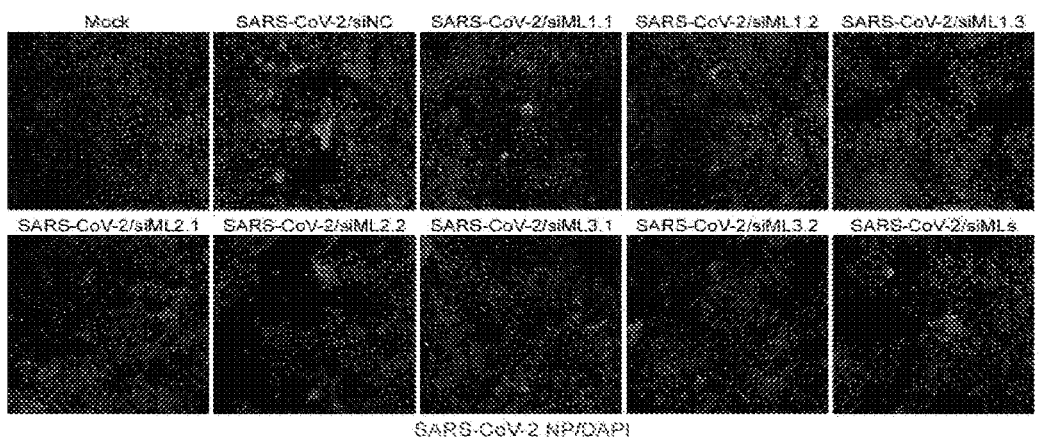
Figure 14B:
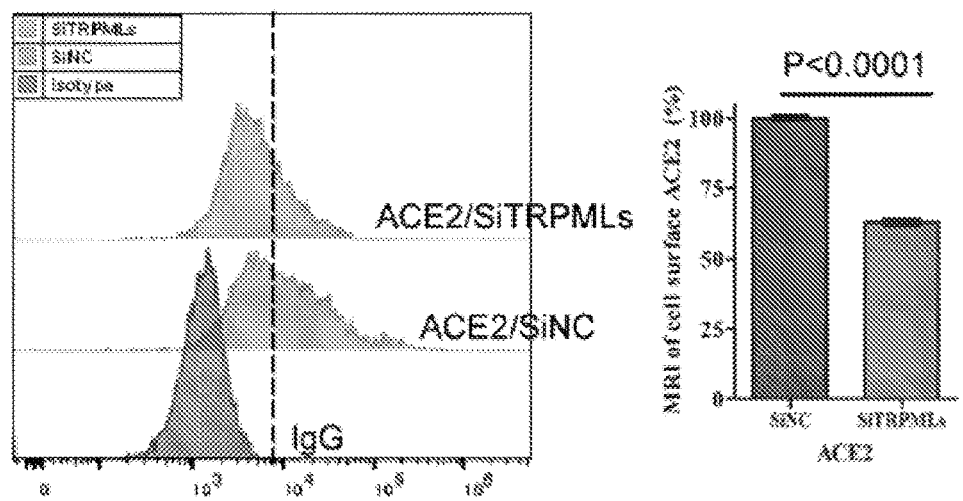
Figure 14C:
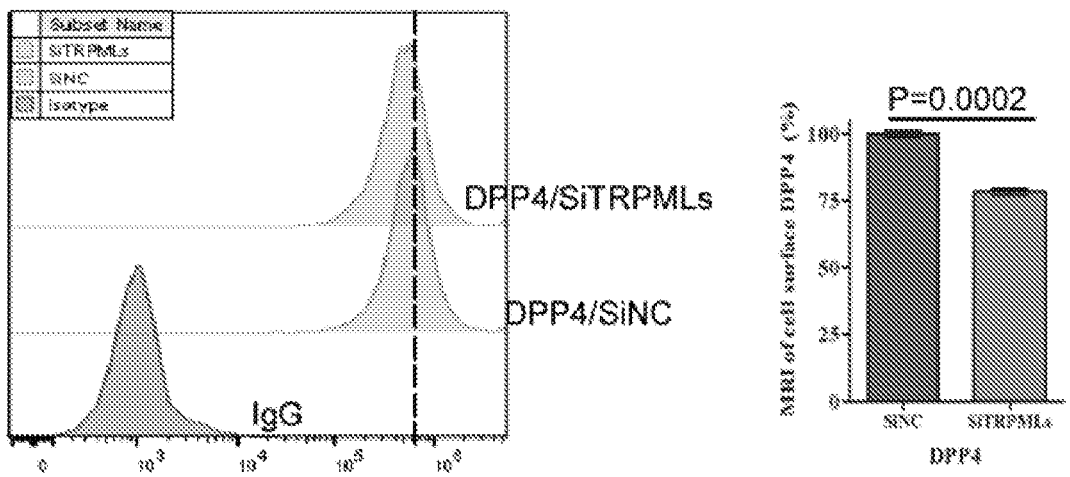
Figure 14D:
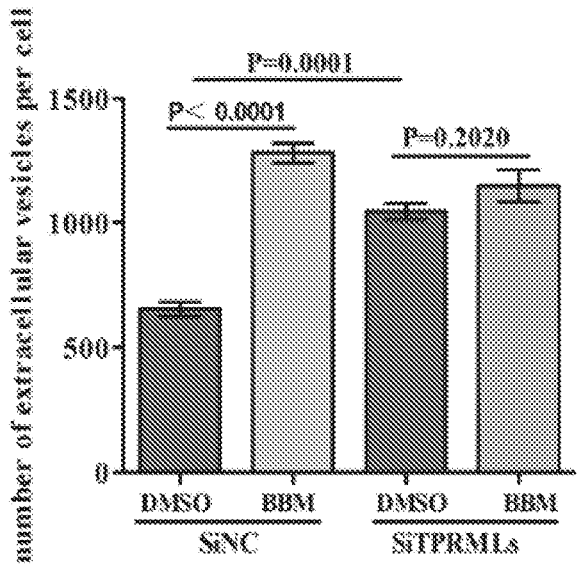
Figure 14E:
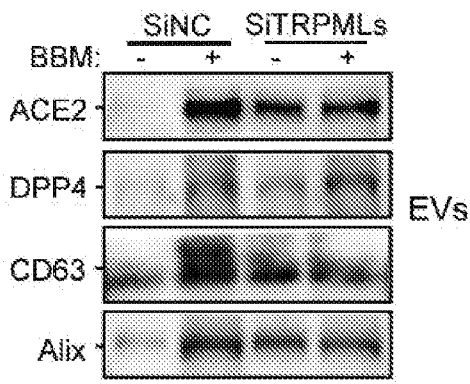

Finally, the inventors assessed the role of TRPMLs in SARS-CoV-2 infection. The inventors knocked down the expression of TRPML1, 2, or 3 individually by respective siRNAs in Huh7 cells, and then infected the control or knockdown cells with SARS-CoV-2, followed by dsRNA staining. The results show that knockdown of TRPML1, TRPML2, or TRPML3 all significantly inhibited SARS-CoV-2 infection in Huh7 cells, manifested by much weaker dsRNA immunofluorescence intensity in TRPMLs-knockdown cells when compared to the control cells (FIG. 14A). Consistently, knockdown of TRPMLs significantly increased EVs secretion in Huh7 cells (FIG. 14D), and markedly increased the levels of ACE2, DPP4, CD63 and ALIX in exosomes collected from the knockdown cells when compared to the control cells (FIG. 14E). Also, TRPMLs knockdown significantly decreased the levels of ACE2 and DPP4 at cell surface (FIGS. 14B and 14C). In summary, these data indicate that berbamine compromises the endolysosomal trafficking of ACE2 via inhibition of TRPMLs, and this leads to a decrease in the levels of ACE2 at cell surface, thereby preventing SARS-CoV-2 from entering the host cells.

DISCUSSION

Figure 13A:
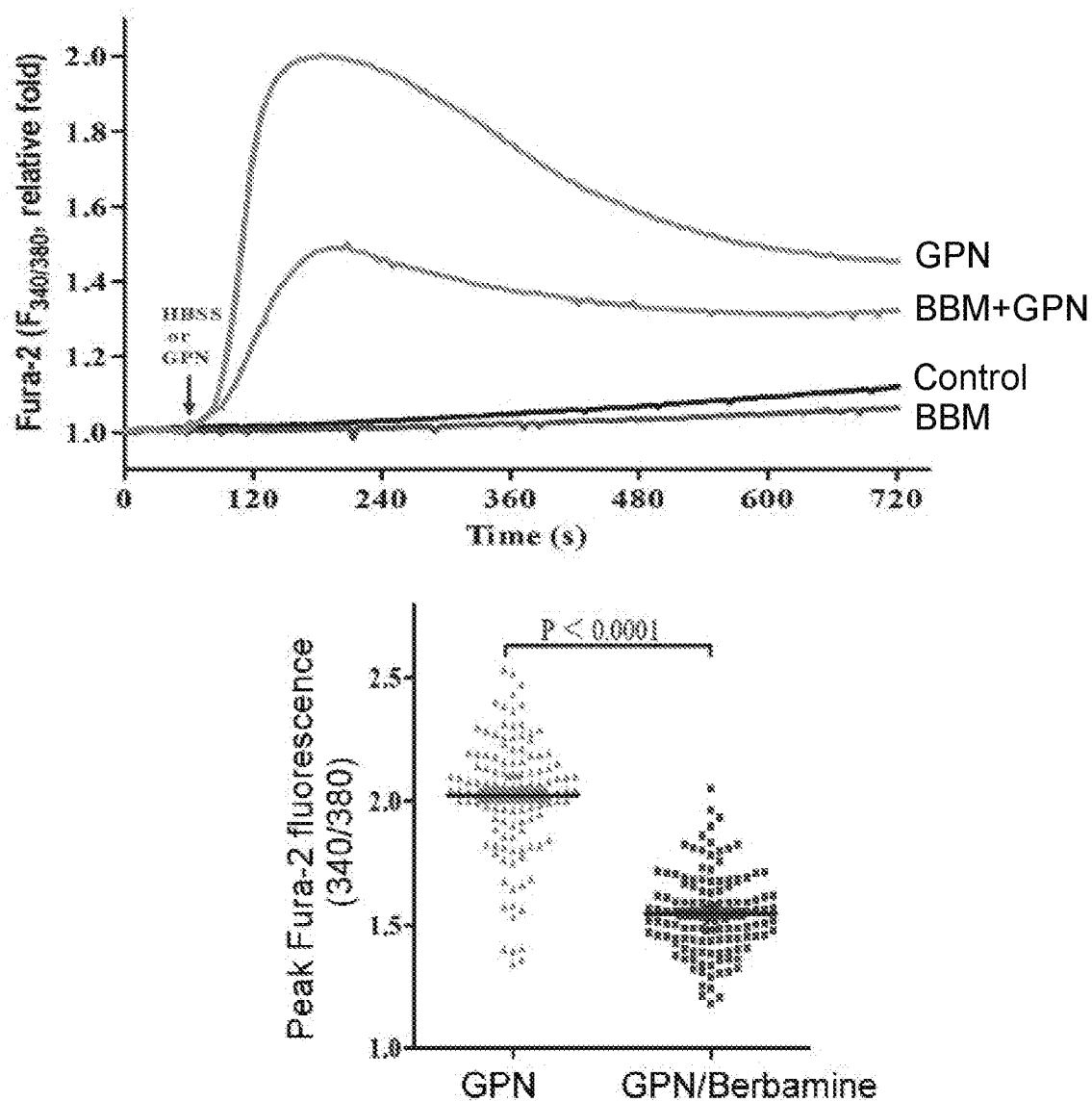
Figure 13B:
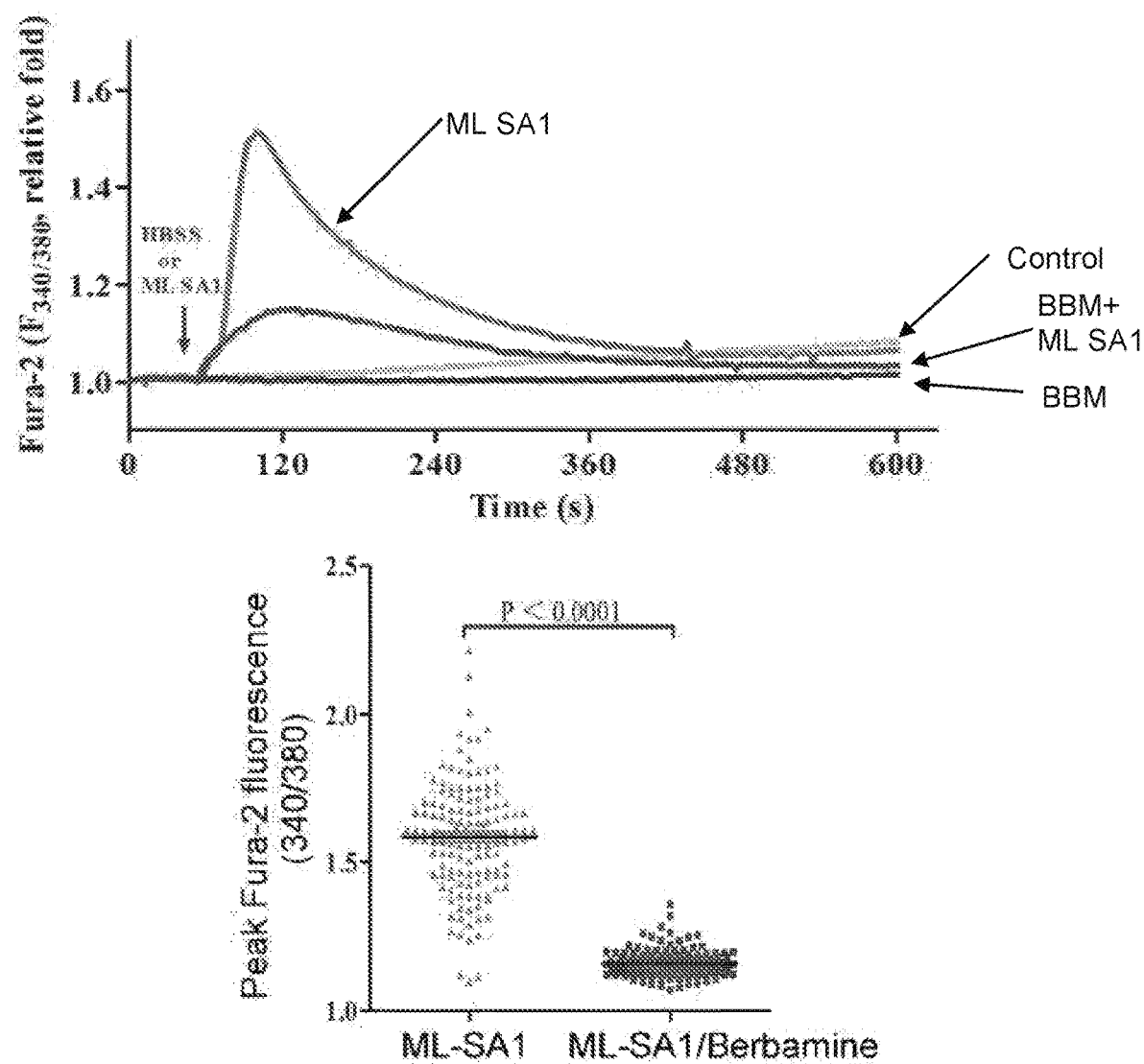
Figure 13C:
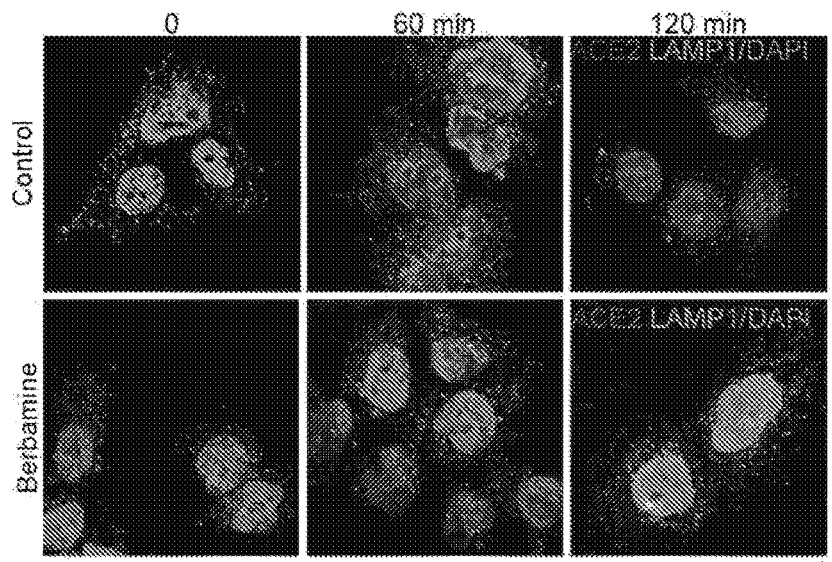
Figure 13D:
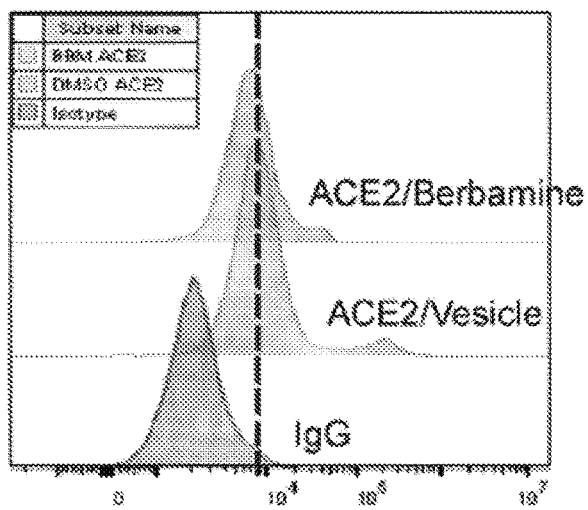
Figure 13D:
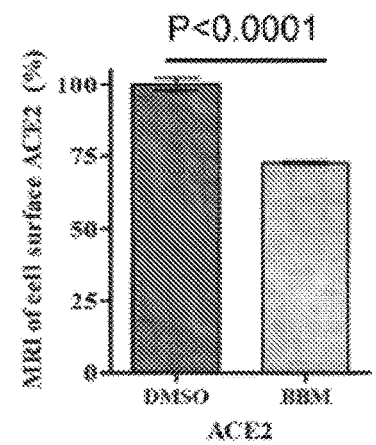
Figure 13E:
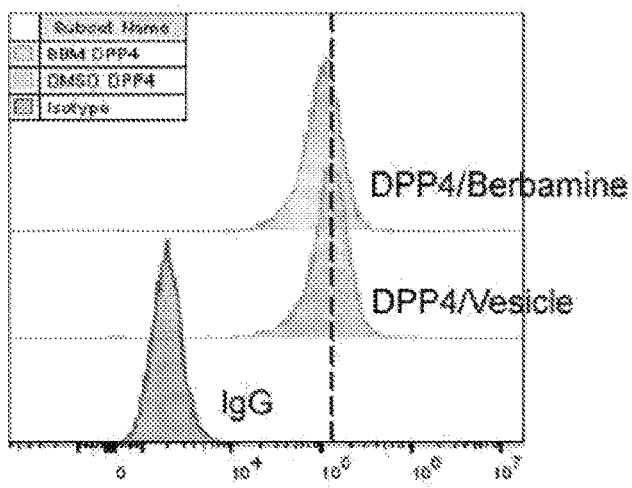
Figure 13E:
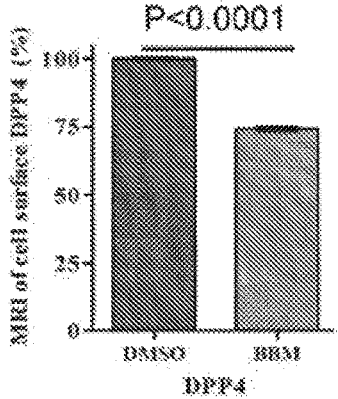
Figure 13F:
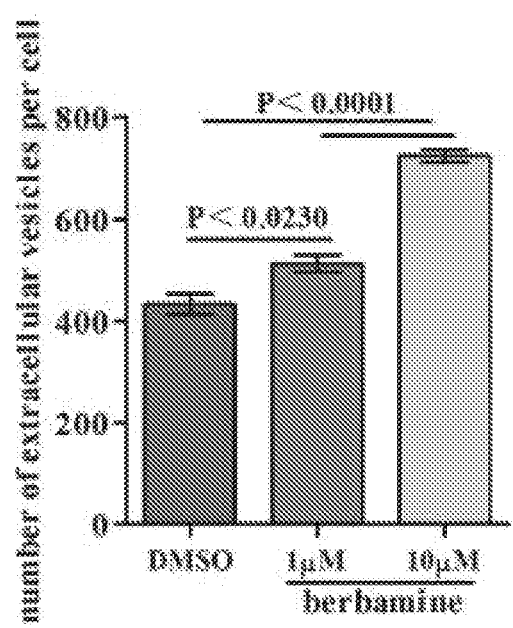
Figure 13G:
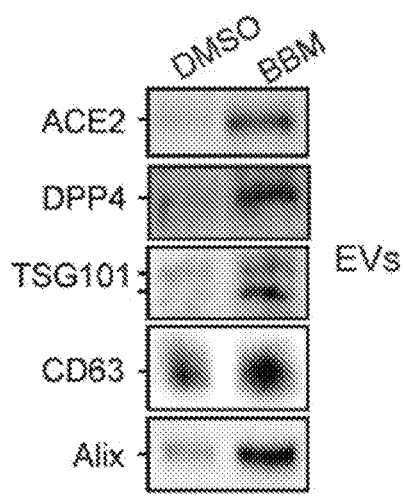

The inventors found that berbamine inhibited TRPML-mediated $Ca^{2+}$ release from lysosomes (FIGS. 13A-13C). Although whether berbamine directly inhibits TRPMLs remains to be determined, it did compromise the endolysosomal trafficking of ACE2 (FIG. 13D), and promoted its secretion out of cells via EVs (FIGS. 13F and 13G). This resulted in the decreased levels of ACE2 at cell surface (FIG. 13D), and led to the failure of SARS-CoV-2 to enter berbamine-treated host cells (FIG. 12B). TRPLMs knockdown also induced exosome secretion (FIG. 14D), reduced the levels of ACE2 at cell surface (FIG. 14B), and prevented the infection of SARS-CoV-2 (FIG. 14A). These knockdown phenotypes were similar to berbamine, suggesting that the inhibitory effect of berbamine on TRPMLs is, at least partially, responsible for its anti-viral activity. Notably, although berbamine or TRPMLs knockdown significantly decreased, but not abolished, the levels of ACE2 or DPP4 at plasma membrane (FIGS. 13D, 13E, 14B, and 14C), they did very effectively inhibit SARS-CoV-2 or MERS-CoV infection (FIGS. 12C-12F, and 14A).

These results suggest that when the levels of ACE2 or DPP4 at the plasma membrane drop to certain levels, these CoVs could not effectively infect the host cells.

The inventors showed that berbamine or TRPMLs knockdown not only inhibited the endolysosomal degradation of ACE2, but also induced the secretion of exosomes containing ACE2 (FIGS. 13 and 14). Interfering endolysomal trafficking has been shown to promote the exosome release, and this is likely due to the increased formation of ILVs in the accumulated late endosomal MVBs, and/or increased fusion between MVBs and the plasma membrane, resulting in the increased release of exosomes. It is also possible that berbamine might regulate the core molecular machinery of exosome secretion or biogenesis to increase exosome secretion. It is possible that berbamine might regulate CaMKII or NF-kB, to inhibit other parts of viral life cycle in the host cells, e.g. replication, packaging, or/and release of the viral particles, in addition to the viral entry. Berbamine might also inhibit TRPMLs-induced autophagy to control SARS-CoV-2 infection.

The results herein indicate that berbamine possesses great potential to be developed into an effective therapeutic agent for the prevention and/or treatment of MERS-CoV and SARS-CoV-2 infections.

MATERIALS AND METHODS

Cell culture and virus propagation-VeroE6, Huh7 and HEK293T cells were maintained in DMEM (Gibco, 12800082) containing 10% fetal bovine serum (Gibco, 10500064) and 100 U/ml of penicillin/streptomycin.

Immunofluorescence Staining

Cells were fixed with 4% paraformaldehyde (PFA) solution, blocked with PBS containing 5% normal donkey serum and 0.3% Triton™ X-100, and then incubated with primary antibody followed by the appropriate fluorescent secondary antibody. To label the receptors on the plasma membrane, live cells were incubated with the primary antibody in PBS (+1% BSA) on ice for 90 min, followed by incubation with the fluorescent secondary antibody on ice. Images were captured with a Carl Zeiss LSM 880 confocal microscope using a 63×oil objective lens. The primary antibodies used in these experiments are shown in FIG. 16.

Western Blot Analysis

The Bradford assay (Bio-RAD) was performed to measure the protein concentration of cell lysates. An equal amount of protein sample was loaded onto 8%-12% SDS-PAGE gels for electrophoresis. The proteins were then transferred to a PVDF membrane (Millipore), blocked with 5% non-fat milk, and blotted with primary and secondary antibodies. The primary antibodies used for immunoblotting are shown in FIG. 16.

The Anti-Virus Activity of Drugs

For anti-SARS-CoV-2 activity of berbamine, Vero-E6 cells were pre-treated with berbamine at a titration of different concentrations (0-75 µM) for 6 hours. Then, the cells were washed with PBS and inoculated with SARS-CoV-2 at 0.01 MOI for 2 hours. At 2 hours post infection (hpi), the cells were washed with PBS and treated with berbamine at a titration of different concentrations (0-75 µM). At 24 hpi, 100 µL of viral supernatant was lysed and proceed to total RNA extraction using the QIAamp viral RNA mini kit (Qiagen, Hilden, Germany). The extracted RNA was then used to quantify the replication of SARS-CoV-2 using real-time quantitative RT-PCR (qRT-PCR).

Purification of extracellular vesicles from the culture medium-A549 cells or Huh7 cells were grown in 15-cm dishes to ~80% confluency. The cells were then rinsed with PBS and incubated in EV-depleted complete medium containing DMSO or berbamine (25 µM) for 48 h. The supernatant was then collected and subjected to sequential centrifugation steps at different centrifugal forces (g) to remove the intact cells, dead cells or cell debris. After each centrifugation, the supernatant was transferred into a new 50 mL tube and the pellet was discarded. Finally, the supernatant was subjected to ultracentrifugation at 120,000×g for 90 min, and the pellet (now containing the extracellular vesicles) was washed with PBS and subjected to another ultracentrifugation at 120,000×g for 90 min. Finally, the exosome pellet collected and used for immunoblot analysis.

Intracellular Ca2+ Measurements

HeLa cells were grown in 24-well plates to ~80% confluency. The cells were then loaded with HBSS (Gibco, 14025092) containing 4 µM Fura-2 AM (Invitrogen, F1221) and 0.4% Pluronic™ F-127 (Invitrogen, P3000MP) at room temperature for 30 min. The cells were then washed with $Ca^{2+}$-free HBSS containing 2 mM EGTA and incubated in $Ca^{2+}$-free HBSS in the presence or absence of berbamine (10 µM) at room temperature for another 30 min. Fluorescence images were acquired at 3 s intervals by alternate excitation at 340 nm and 380 nm with emission at 510 nm using a Nikon Eclipse Ti-S Calcium imaging system. Approximately 1 min after live cell imaging, 200 µM GPN (Abcam, ab145914) or 25 µM ML-SA1 (Tocris Bioscience, 4746) was added to the cells to trigger Ca2+ release from the lysosomes.

Small Interference RNA (siRNA)

Cells were transfected with siRNAs against respective genes (Table S1) using Lipofectamine 3000 according to the manufacturer's instructions. The knockdown efficiency was validated by immunoblot analysis or qRT-PCR.

Statistical Analysis

Data are presented as mean±S.E.M. Statistically significant differences were determined by the Student's t-test and $P<0.05$ was considered to be statistically significant.

The invention claimed is:

1. A method of preventing or treating a subject suffering from a coronavirus infection caused by severe acute respiratory syndrome coronavirus 2, by administering an effective amount of berbamine or its analogue to the subject, wherein berbamine has a structure of Formula (I):

Formula (I)

2. The method of claim 1, wherein the subject is a mammal and the berbamine or its analogue is administered to the subject at a dose of about 20 mg/kg to about 50 mg/kg.

3. A method of inhibiting the entry of a coronavirus into host cells, comprising contacting the host cells with an effective amount of berbamine or its analogue, wherein berbamine has a structure of Formula (I):

Formula (I)

and wherein the coronavirus is severe acute respiratory syndrome coronavirus 2.

4. The method of claim 3, wherein berbamine or its analogue inhibits the entry of SARS-CoV-2 in host cells of a subject.

5. The method of claim 3, wherein the analogue of berbamine has a structure of Formula (Ib):

Formula (Ib)

wherein $R_1$, $R_2$, $R_3$, $R_4$ are independently selected from a hydrogen atom, a C1-C3 alkyl group, a halogen atom, and a nitrogen containing group, with the proviso that the analogue is not tetrandrine.

* * * * *